United States Patent
Gottardis et al.

(10) Patent No.: US 11,986,470 B2
(45) Date of Patent: *May 21, 2024

(54) METHODS OF TREATING PROSTATE CANCER

(71) Applicant: Janssen Pharmaceutica NV, Beerse (BE)

(72) Inventors: Marco Gottardis, Princeton, NJ (US); Rebecca Hawkins, Harleysville, PA (US); Linda A. Snyder, Pottstown, PA (US); Douglas H. Yamada, Philadelphia, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/466,547

(22) Filed: Sep. 13, 2023

(65) Prior Publication Data

US 2024/0000766 A1    Jan. 4, 2024

Related U.S. Application Data

(63) Continuation of application No. 17/989,329, filed on Nov. 17, 2022, which is a continuation of application No. 17/528,017, filed on Nov. 16, 2021, which is a continuation of application No. 16/131,772, filed on Sep. 14, 2018, now Pat. No. 11,207,311, which is a continuation of application No. 15/663,082, filed on Jul. 28, 2017, now abandoned.

(Continued)

(51) Int. Cl.
*A61K 31/454* (2006.01)
*A61K 9/00* (2006.01)
*A61P 13/08* (2006.01)
*A61P 35/00* (2006.01)
*A61P 35/04* (2006.01)

(52) U.S. Cl.
CPC .......... *A61K 31/454* (2013.01); *A61K 9/0053* (2013.01); *A61P 13/08* (2018.01); *A61P 35/00* (2018.01); *A61P 35/04* (2018.01)

(58) Field of Classification Search
CPC ................ A61K 31/454; A61K 9/0053; A61K 2300/00; A61K 31/573; A61K 31/58; A61K 45/06; A61P 35/00; A61P 13/08; A61P 35/04
See application file for complete search history.

(56) References Cited

U.S. PATENT DOCUMENTS 4,717,721 A    1/1988 Deluca et al.
4,851,401 A    7/1989 Deluca et al.
(Continued)

FOREIGN PATENT DOCUMENTS

CN    101528308 A    9/2009
CN    104306977 A    1/2015
(Continued)

OTHER PUBLICATIONS

"Amended marketing authorization for Zytiga", European Commission, Nov. 9, 2016, pp. 74.
(Continued)

*Primary Examiner* — Savitha M Rao
(74) *Attorney, Agent, or Firm* — BakerHostetler

(57) ABSTRACT

Disclosed are methods of treating prostate cancer by administering niraparib to a human in need thereof.

22 Claims, 5 Drawing Sheets

Niraparib inhibits the growth of human prostate tumor cell lines in vitro.

Related U.S. Application Data

(60) Provisional application No. 62/369,239, filed on Aug. 1, 2016, provisional application No. 62/368,466, filed on Jul. 29, 2016.

(56) References Cited

U.S. PATENT DOCUMENTS

| | | |
|---|---|---|
| 4,857,518 A | 8/1989 | Deluca et al. |
| 4,866,048 A | 9/1989 | Calverley et al. |
| 5,120,722 A | 6/1992 | Baggiolini et al. |
| 5,145,846 A | 9/1992 | Baggiolini et al. |
| 5,190,935 A | 3/1993 | Binderup et al. |
| 5,237,110 A | 8/1993 | Deluca et al. |
| 5,411,949 A | 5/1995 | Neef et al. |
| 5,446,035 A | 8/1995 | Neef et al. |
| 5,547,947 A | 8/1996 | Dore et al. |
| 5,604,213 A | 2/1997 | Barrie et al. |
| 5,618,807 A | 4/1997 | Barrie et al. |
| 5,688,977 A | 11/1997 | Sisti et al. |
| 6,087,350 A | 7/2000 | Johnson et al. |
| 6,310,226 B1 | 10/2001 | Calverley et al. |
| 6,521,608 B1 | 2/2003 | Henner et al. |
| 6,559,139 B1 | 5/2003 | Johnson et al. |
| 6,872,568 B1 | 3/2005 | Ni et al. |
| 7,071,333 B2 | 7/2006 | Combs et al. |
| 7,256,193 B2 | 8/2007 | Kyle et al. |
| 7,482,334 B2 | 1/2009 | Frincke et al. |
| 7,547,687 B2 | 6/2009 | Reading et al. |
| 7,709,517 B2 | 5/2010 | Sawyers et al. |
| 8,071,623 B2 | 12/2011 | Jones et al. |
| 8,183,274 B2 | 5/2012 | Sawyers et al. |
| 8,436,185 B2 | 5/2013 | Foley et al. |
| 8,658,128 B2 | 2/2014 | Altschul et al. |
| 8,822,438 B2 | 9/2014 | Auerbach et al. |
| 9,114,147 B2 | 8/2015 | Altschul et al. |
| 9,126,941 B2 | 9/2015 | Sawyers et al. |
| 9,295,680 B2 | 3/2016 | Altschul et al. |
| 9,314,473 B2 | 4/2016 | Altschul et al. |
| 9,320,747 B1 | 4/2016 | Altschul et al. |
| 9,598,459 B2 | 3/2017 | Altschul et al. |
| 9,636,351 B2 | 5/2017 | Altschul et al. |
| 9,642,866 B2 | 5/2017 | Altschul et al. |
| 9,855,284 B2 | 1/2018 | Altschul et al. |
| 9,861,643 B2 | 1/2018 | Altschul et al. |
| 10,058,563 B2 | 8/2018 | Altschul et al. |
| 10,076,528 B2 | 9/2018 | Altschul et al. |
| 10,231,982 B2 | 3/2019 | Altschul et al. |
| 10,238,666 B2 | 3/2019 | Altschul et al. |
| 10,517,881 B2 | 12/2019 | Altschul et al. |
| 10,537,586 B2 | 1/2020 | Altschul et al. |
| 11,040,037 B2 | 6/2021 | Altschul et al. |
| 11,207,311 B2 | 12/2021 | Gottardis et al. |
| 11,224,599 B2 | 1/2022 | Altschul et al. |
| 11,364,252 B2 | 6/2022 | Altschul et al. |
| 11,576,921 B2 | 2/2023 | Altschul et al. |
| 2002/0128240 A1 | 9/2002 | Mazess |
| 2003/0083231 A1 | 5/2003 | Ahlem et al. |
| 2003/0119795 A1 | 6/2003 | Henner et al. |
| 2004/0138187 A1 | 7/2004 | Reading et al. |
| 2005/0020546 A1 | 1/2005 | Laidlaw et al. |
| 2005/0054620 A1 | 3/2005 | Koeffler et al. |
| 2005/0101581 A1 | 5/2005 | Reading et al. |
| 2005/0233958 A1 | 10/2005 | Ni et al. |
| 2006/0003021 A1 | 1/2006 | Strugnell et al. |
| 2006/0003950 A1 | 1/2006 | Strugnell et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0030608 A1 | 2/2006 | Nelson et al. |
| 2007/0203107 A1 | 8/2007 | Frincke et al. |
| 2007/0213309 A1 | 9/2007 | Reading et al. |
| 2007/0265236 A1 | 11/2007 | Reading et al. |
| 2007/0275937 A1 | 11/2007 | Reading et al. |
| 2007/0275938 A1 | 11/2007 | Reading et al. |
| 2008/0004286 A1 | 1/2008 | Wang et al. |
| 2008/0004287 A1 | 1/2008 | Ma et al. |
| 2008/0051375 A1 | 2/2008 | Auerbach et al. |
| 2008/0085873 A1 | 4/2008 | Reading et al. |
| 2008/0138426 A1 | 6/2008 | Hara et al. |
| 2008/0167345 A1 | 7/2008 | Jones et al. |
| 2009/0124587 A1 | 5/2009 | Auerbach et al. |
| 2012/0201747 A1 | 8/2012 | Altschul et al. |
| 2014/0107086 A1 | 4/2014 | Theise et al. |
| 2014/0315920 A1 | 10/2014 | Virca et al. |
| 2014/0336154 A1 | 11/2014 | Do et al. |
| 2014/0336157 A1 | 11/2014 | Auerbach et al. |
| 2015/0344968 A1 | 12/2015 | Johnson |
| 2015/0366881 A1 | 12/2015 | Altschul et al. |
| 2015/0366882 A1 | 12/2015 | Altschul et al. |
| 2016/0113948 A1 | 4/2016 | Altschul et al. |
| 2016/0160294 A1 | 6/2016 | Wilcoxen et al. |
| 2016/0279148 A1 | 9/2016 | Altschul et al. |
| 2016/0279149 A1 | 9/2016 | Altschul et al. |
| 2017/0051007 A1 | 2/2017 | Altschul et al. |
| 2017/0128465 A1 | 5/2017 | Altschul et al. |
| 2017/0202859 A1 | 7/2017 | Altschul et al. |
| 2017/0232005 A1 | 8/2017 | Altschul et al. |
| 2018/0017438 A1 | 1/2018 | Crohn et al. |
| 2018/0028521 A1 | 2/2018 | Gottardis et al. |
| 2018/0117066 A1 | 5/2018 | Altschul et al. |
| 2018/0185392 A1 | 7/2018 | Altschul et al. |
| 2018/0296574 A1 | 10/2018 | Snyder et al. |
| 2018/0325920 A1 | 11/2018 | Altschul et al. |
| 2018/0360852 A1 | 12/2018 | Altschul et al. |
| 2019/0022079 A1 | 1/2019 | Gottardis et al. |
| 2019/0134062 A1 | 5/2019 | Altschul et al. |
| 2019/0151335 A1 | 5/2019 | Altschul et al. |
| 2019/0381038 A1 | 12/2019 | Altschul et al. |
| 2020/0101087 A1 | 4/2020 | Altschul et al. |
| 2021/0353623 A1 | 11/2021 | Altschul et al. |
| 2021/0361675 A1 | 11/2021 | Altschul et al. |
| 2022/0298203 A1 | 9/2022 | Altschul et al. |
| 2023/0142627 A1 | 5/2023 | Altshul et al. |

FOREIGN PATENT DOCUMENTS

| | | |
|---|---|---|
| DE | 10061137 A1 | 6/2002 |
| EP | 0413270 A2 | 2/1991 |
| EP | 0912535 A1 | 5/1999 |
| EP | 0914116 A1 | 5/1999 |
| EP | 1140192 A2 | 10/2001 |
| EP | 1336602 A1 | 8/2003 |
| EP | 1379246 A1 | 1/2004 |
| EP | 1385514 A1 | 2/2004 |
| EP | 1385515 A1 | 2/2004 |
| EP | 1385518 A1 | 2/2004 |
| EP | 1423381 A1 | 6/2004 |
| EP | 1463733 A2 | 10/2004 |
| EP | 1466628 A1 | 10/2004 |
| EP | 1487829 A1 | 12/2004 |
| EP | 1515949 A1 | 3/2005 |
| EP | 1556354 A2 | 7/2005 |
| EP | 1562932 A1 | 8/2005 |
| EP | 1562936 A2 | 8/2005 |
| EP | 1572299 A1 | 9/2005 |
| EP | 1583524 A1 | 10/2005 |
| EP | 1583763 A1 | 10/2005 |
| EP | 1598338 A1 | 11/2005 |
| EP | 1598339 A1 | 11/2005 |
| EP | 1598340 A1 | 11/2005 |
| EP | 1631285 A1 | 3/2006 |
| EP | 1307197 B1 | 4/2006 |
| EP | 1648879 A1 | 4/2006 |
| EP | 1664016 A2 | 6/2006 |
| EP | 1664041 A1 | 6/2006 |
| EP | 1674479 A1 | 6/2006 |
| EP | 1676577 A1 | 7/2006 |
| EP | 1803718 A1 | 7/2007 |
| EP | 1810970 A1 | 7/2007 |
| EP | 1412368 B1 | 8/2007 |
| EP | 1673092 B1 | 8/2007 |
| EP | 1862458 A2 | 12/2007 |
| EP | 1867644 A1 | 12/2007 |
| EP | 1918279 A2 | 5/2008 |

(56) References Cited

FOREIGN PATENT DOCUMENTS

| | | |
|---|---|---|
| EP | 1927858 A1 | 6/2008 |
| EP | 1930322 A1 | 6/2008 |
| EP | 1942106 A1 | 7/2008 |
| EP | 1975164 A2 | 10/2008 |
| EP | 2336120 A1 | 6/2011 |
| EP | 2478907 A2 | 7/2012 |
| EP | 2061561 B1 | 7/2013 |
| EP | 2805945 A1 | 11/2014 |
| EP | 2007733 B1 | 5/2016 |
| JP | 2003-525254 A | 8/2003 |
| JP | 2006-515623 A | 6/2006 |
| JP | 2010-501575 A | 1/2010 |
| JP | 2010-515715 A | 5/2010 |
| WO | 92/00992 A1 | 1/1992 |
| WO | 93/20097 A1 | 10/1993 |
| WO | 95/09178 A1 | 4/1995 |
| WO | 01/64251 A2 | 9/2001 |
| WO | 01/81364 A1 | 11/2001 |
| WO | 01/93836 A2 | 12/2001 |
| WO | 02/03286 A1 | 1/2002 |
| WO | 02/32861 A2 | 4/2002 |
| WO | 02/53138 A2 | 7/2002 |
| WO | 02/85355 A1 | 10/2002 |
| WO | 02/85361 A1 | 10/2002 |
| WO | 02/91993 A2 | 11/2002 |
| WO | 2002/102783 A1 | 12/2002 |
| WO | 03/20699 A2 | 3/2003 |
| WO | 03/22835 A1 | 3/2003 |
| WO | 03/37252 A2 | 5/2003 |
| WO | 03/39460 A2 | 5/2003 |
| WO | 03/86388 A1 | 10/2003 |
| WO | 03/86404 A1 | 10/2003 |
| WO | 03/92595 A2 | 11/2003 |
| WO | 2004/012699 A2 | 2/2004 |
| WO | 2004/012700 A2 | 2/2004 |
| WO | 2004/016753 A2 | 2/2004 |
| WO | 2004/037269 A1 | 5/2004 |
| WO | 2004/041164 A2 | 5/2004 |
| WO | 2004/062620 A2 | 7/2004 |
| WO | 2005/016236 A2 | 2/2005 |
| WO | 2005/021487 A1 | 3/2005 |
| WO | 2005/107801 A2 | 11/2005 |
| WO | 2006/004917 A2 | 1/2006 |
| WO | 2006/021776 A1 | 3/2006 |
| WO | 2006/027266 A1 | 3/2006 |
| WO | 2006/050402 A1 | 5/2006 |
| WO | 2006/081152 A2 | 8/2006 |
| WO | 2006/116217 A2 | 11/2006 |
| WO | 2006/116716 A2 | 11/2006 |
| WO | 2007/014327 A1 | 2/2007 |
| WO | 2008/024484 A1 | 2/2008 |
| WO | 2008/039254 A2 | 4/2008 |
| WO | 2008/062466 A2 | 5/2008 |
| WO | 2008/084261 A1 | 7/2008 |
| WO | 2008/100985 A2 | 8/2008 |
| WO | 2008/109740 A2 | 9/2008 |
| WO | 2008/127290 A2 | 10/2008 |
| WO | 2009/087381 A1 | 7/2009 |
| WO | 2012/009475 A1 | 1/2012 |
| WO | 2012/106514 A2 | 8/2012 |
| WO | 2014/089324 A1 | 6/2014 |
| WO | 2015/164586 A1 | 10/2015 |
| WO | 2016/094391 A1 | 6/2016 |
| WO | 2017/023694 A1 | 2/2017 |
| WO | 2018/067520 A2 | 4/2018 |
| WO | 2019/074536 A1 | 4/2019 |

OTHER PUBLICATIONS

"CB-7630 Shows Activity in Prostate Cancer Trials," Daily Essentials (2007).
"Clinical Trials: What you need to know", American cancer society, Aug. 18, 2020, pp. 1-29.
"Cougar Bioledmology Announces Positive CB7630 Phase I Data at the AACR Innovations in Prostate Cancer Research Conference," News Release, available at http://www.cougarbiotechnology.com (2006).
"Cougar Bioledmology Announces Presentation of Positive Phase I and Phase II Data at ASCO Prostate Cancer Symposium," News Release, available at hitp://www.cougarbiotechnology.com (2007).
"Cougar Biotechnolagy Presents Positive CB7630 Phase I and Phase II Data at ASCO 2008 Genitourinary Cancers Symposium," News Release, available at http://www.cougarbiotechnology.com (2008).
"Cougar Biotechnology Announces Acceptance of CTA for Abiraterone Acetate," News Release, available at: http:www.cougarbiotechnolagy.com (2005).
"Cougar Biotechnology Announces Initiation of Phase I Trial for CB7630 (Abiratemne Acetate)," News Release, available at http:I/v,wvv.cougarbiotechnology.com (2006).
"Cougar Biotechnology Announces Initiation of Phase III Trial of CB7630 (Abiraterone Acetate)," News Release, available at http://www.caugarbiotechnology.com (2008).
"Cougar Biotechnology Announces Initiation of Phase I/II Trial for CB7630 (Abiratemne Acetate)." News Release, available at: http://www.caugarbiotechnology.com (2005).
"Cougar Biotechnology Announces Initiation of Phase I/II Trial of CB7630 (Abiraterone Acetate) in Advanced Breast Cancer Patients," News Release, available at http://www.cougarbiotechnology.com (2008).
"Cougar Biotechnology Announces Positive CB7630 Phase I Data Presented at the National cancer Research Institute Conference," News Release available at: http://www.cougarbiotechnology.com (2006).
"Cougar Biotechnology Announces Presentation of Positive CB7630 (Abiraterone Acetate) Phase II Data at.ASCO 2009 Genitourinary Cancers Symposium," News Release, available at http://www.cougarbiotechnology.com (2009).
"Cougar Biotechnology Announces Presentation of Positive CB7630 Clinical Data at AUA Annual Meeting," News Release, available at http://www.cougarbiotechnology.com (2007).
"Cougar Biotechnology Announces Presentation of Positive CB7630 Clinical Data at ESMO Conference," New-s Release, available at: http://www.cougarbiotechnology.com (2007).
"Cougar Biotechnology Announces Presentation of Positive CB7630 Phase I Clinical Data at ASCO 2008 Genitourinary Cancers Symposium," News Release, available at http://www.cougarbiotechnology.com (2008).
"Cougar Biotechnology Armounces CB7630 Phase I Data to be Presented at National Cancer Research Institute Conference," News Release (Sep. 27, 2006), available at http://www.cougarbiotechnology.com (2006).
Cougar Biotechnology Initiales Phase II Trial of C87630 (Abiraferone Acetate), News Release, available at: http://www.cougarbiotechnology.com (2006).
"Cougar Biotechnology Presents CB7630 Phase I Clinical Data at the 2005 Prostate Cancer Symposium," Nevvs Release, available at http/www.cougarbiotechnology.com (2005).
"Cougar Biotechnology Presents Positive CB7630 (Abiraterone Acetate) Phase I and Phase II Data at ASCO 200B Annual Meeting," News Release, available at http://www.cougarbiotechnology.com (2008).
"Cougar Biotechnology Presents Positive CB7630 Clinical Data at AACR Annual Meeting Late-Breaking Clinical Trials Session," News Release, available at: http:www.cougarbiotechnology.com (2007).
"Cougar Biotechnology Presents Positive CB7630 Phase II Data at Chemotherapy Foundation Symposium;" News Release, available at: htlp://www.cougarbiotechnology.com (2007).
"Cougar Biotechnology Presents Positive CB7630 PhaseII Data at EORTC-NCI-AACR Symposium," News Release, available at: http://www.cougarbiotechnology.com (2008).
"Cougar Biotechnology to Present Clinical Data on CB7630 (Abiratemne Acetate) at American Society of Clinical Oncology 2008 Annual Meeting." Nevvs Release, available at http://www.cougarbiotechnology.com (2008).

(56) References Cited

OTHER PUBLICATIONS

"Cougar Biotechoology Announces Agreement with FDA on Special Protocol Assessrnent for PhaseIII Trial of C87630 (Abi.raternne Acetate) in Chemotherapy Naive Castration Resistant Prostate Cancer Patients". News. Release, available at http:/www. cougarbiotechnology.com (2008).

"Cougar Biotedmology Presents CB7630 Phase I Data at Prostate Ganeer Foundation Scientific Retreat." News Release, available at: http-//www. cougarbioiechnology.com (2004).

"Final Written Decision", United States Patent and Trademark Office Before the Patent Trial and Appeal Board, Case No. IPR2016,00286 U.S. Pat. No. 8,822,A38 B2, Jan. 17, 2018, 48 pages.

"Final Written Decision", United States Patent and Trademark Office Before the Patent Trial and Appeal Board, Case No. IPR2016-01332 U.S. Pat. NO. 8,822,438 B2, Jan. 17, 2018, 50 page.

"Full Prescribing Information and Patient Information for ZEJULA", Mar. 2017, pp. 1-19.

"Marketing authorization for Zytiga", European Commission, Sep. 5, 2011, pp. 31.

"Monetizing Focus: Tesaro Adds Runway By Out-licensing Niraparib In Prostate Cancer", Pink sheet, Apr. 6, 2016, pp. 1-3.

"OncoGenex Announces Top-Line Survival Results of Phase 3 Synergy Trial Evaluating Custirsen for Metastatic Castrate-Resistant Prostate Cancer", Janssen Exhibit 2077, *Amerigen* vs. *Janssen*, filed for Case#IPR2016-00286, Aptil 28, 2014, 2 Page.

"Ph Il Study to Evaluate Olaparib With Abiraterone in Treating Metastatic Castration Resistant Prostate Cancer", NCT01972217, First Posted Oct. 30, 2013.

"Positive Phase II Data on Cougar Biotechnology's CB7630 Presented at Prostate Cancer Foundation Scientific Retreat," News Release, available at http://www.cougarbiotechnology.com (2008).

"Study Status and Contacts/Locations History of Changes for Study: NCT02924 766 A Safety and Pharmacokinetics Study of Niraparib Plus Apalutamide in Men With Metastatic Castratio•• Resistant Prostate Cancer (BEDIVERE)", Retrieved from https://clinicaltrials.gov/study/NCT02924766?tab=history&a=1#StudyPageTop,(20230321),XP093033276%5BA%5D1-21.

"Tesaro Announces Global Prostate Cancer Collaboration and Licensing Agreement With Janssen", Apr. 6, 2016, pp. 1-2.

A Phase 3, Randomized, Double-Blind, Placebo-Controlled Study of Abiraterone Acetate (CB7630) Plus Prednisone in Patients with Metastatic Castration-Resistant Prostate Cancer Who Have Failed Docetaxel-Based Chemotherapy, Clinical Genitourinary Cancer, vol. 6(2): 140 (2008).

Abad L et al., "Male pseudohermaphroditism with 17 alpha-hydroxylase deficiency", A case report. Br J Obstet Gynaecol Dec. 1980, vol. 87 No. 12 pp. 1162-1165.

Abida, Wassim, et al., "Targeting DNA Repair in Prostate Cancer", Journal of Clinical Oncology, American Society of Clinical Oncology, Apr. 1, 2018, vol. 36, No. 10, pp. 1017-1021.

Abiraternne Acetate: Abbreviated Clinical Study Report Synopsis COU-AA-BE (Doc. EDMS-ERI-13494974:2.0) (BE Synopsisx) 2010, 5 pages.

Abiraterone: A Story of Scientific Innovation and Commercial Partnership, http://www.icr.ac.uk/news-features/latestfeatures/abiraterone-a-story-0f-scientific-innovation-andcommercial-artnership, Dec. 19, 2016, pp. 1-14.

About Zytiga (Registered) Arbiraterone acetate, retrived from https://www.zytiga.com/choosing-zytiga#how-zytiga-works, on Jul. 25, 2017, 7 pages.

Acadamy of Managed Care Pharmacy (AMCP) Nexus 2016, National Harbor, MD, USA; Oct. 3-6, 2016 filed for Janssen IPR2016-01332.

Aggarwal et al., "Development of Abiraterone Acetate, a 17-alpha Hydroxylase C17,20-Lyase Inhibitor as a Secondary Hormonal Therapy in Prostate Cancer," Update on Cancer Therapeutics, vol. 2:171-175 (2007).

Altman et al., "The Revised Consort Statement for Reporting Randomized Trials: Explanation and Elaboration", Annals of Internal Medicine vol. 134, No. 8, Apr. 17, 2001, pp. 663-694.

Anlonarakis and Eisenberger, "Phase III Trials With Docetaxel-Based Combinations for Metastatic Castration-Resistant Prostate Cancer: Time to Learn From Past Experiences" Journal of Clinical Oncology, vol. 31, Ne 14. May 10, 2013: pp. 1709-1712.

Annane D et al., "Effect of treatment with low doses of hydrocortisone and fludrocortisone on mortality in patients with septic shock", JAMA, Aug. 21, 2002, vol. 288, No. 7, pp. 862-871.

Anonymous: "NCT00485303—An Efficacy and Safety Study of Abiraterone Acetate and Prednisone in Participants With Prostate Cancer Who Failed Androgen Deprivation and Docetaxel-Based Chemotherapy", Jun. 2007, 3 pages.

Antifungal Treatment Should Be Taken Off the Market, Public Citizen Tells FDA filed for Case# IPR2016-01582 on Feb. 24, 2015, 1 page.

Arlt, W. et al., "Adrenal insufficiency," Lancet, vol. 361 May 31, 2003, pp. 1881-1893.

Efstathiou et al.., "Candidate Predictors of Response to Abiraterone Acetate (AA) in Castrate Resistant Prostate Cancer (CRPC)," 2009 Gemtounnary Cancers Symposium (Feb. 26-28, 2009), abstract Submission (2008).

Efstathiou et al.., Identification of an Androgen Withdrawal Responsive Phenotype in Castrate Resistant Prostate Cancer (CRPC) Patients Treated with Abirnterone Acetate; presentation, 2007.

Efstathiou, Eleni, el al. Effects of Abiraterone Acetate on Androgen Signaling in Castrate-Resistant Prostate Cancer in Bone, American Society of Clinical Oncology, Journal of Clinical Oncology, 2011, pp. 1-8.

Efstathiou, et al., "Enzalutamide in Combination with Abiraterone Acetate in Bone Metastic Castration-resistant Prostate Cancer Patients", Science Direct, European Urology Oncology 3 (2020), 2019 European Association of Urology, Published by Elsevier B.V., pp. 119-127.

Eighteenth Edition Physicians' Desk Reference to Pharmaceutical Specialties and Biologicals, 1964, PDR Published by Medical Economics, Inc. 3 pages.

EMA—Zytiga Product Information, http://www.ema.europa.eu/docs/en_GB/document_library/EPAR_-_product_Information/human/002321/WC500112858pdf, 2016, 37 pages.

Emel Arinc et al., "Molecular Aspects of Monooxygenases and Bioactivation of Toxic Compounds", Series A: Life Sciences vol. 202 Mylan Pharms. Inc., 28 pages.

Endert E. et al.., "Establishment of reference values for endocrine tests. Part IV: Adrenal insufficiency", Netherlands, Journal of Medicine 2005, vol. 63, No. 11, pp. 435-443.

Ergun-Longmire. Berrin et al.., "Two Novel Mutations Found in a Patient with 17a-Hydroxylase Enzyme Deficiency", The Joumal of Clinical Endocrinology & Metabolism (2006), 91(10), p. 4179-4182.

Eric J. Small et al.., "Ketoconazole Retains Activity in Advanced Prostate Cancer Patients With Progression Despite Flutamide Withdrawal", The Journal of Urology, vol. 157 Apr. 1997, pp. 1204-1207.

Eric J. Small et al.., "Second-Line Hormonal therapy for Advanced Prostate Cancer: A Shifting Paradigm", journal of Cliniol Oncology, vol. 15, No. 1 Jan. 1997, pp. 382-388.

Erica L. T. Van Den Akker et al.., "Differential Inhibitlon of 17alpha-hydroxylase and 17,20-lyase activities by three novel missense CYP17 mutations identified in patients with P450c17 deficiency", The Journal of Clinical Endocrinology & Metabolism Dec. 2002, vol. 87 No. 12 pp. 5714-5721.

Erie J. Small et al.., "Antiandrogen Withdraw-al Alone or in Combination With Ketoconazole in Androgen-Independent Prostate Cancer Patients: A Phase III Trial (CALGB9583)", Journal of Clinical Oncology, *Wockhardt* vs. *Janssen*, Flied for Case IPR2016-01582, Janssen Exhibit 2172, on Apr. 3, 2017, 18 pages.

Excerpts from Seifler, Concepts in Medical Physiology, Chapter 34, pp. 540-553, Chapter 37, pp. 606-620 (2005), Filed for Case IPR2016-00286, Janssen Exhibit 2058.

F. Labrie et al.., "Anti-hormone Treatment for Prostate Cancer Relapsing after Treatment with Flutamide and Castration", British Journal of Urology, (1989) 63 ,pp. 634-638.

(56) References Cited

OTHER PUBLICATIONS

Fable Zustovich and Davide Pastorelli, Therapeulic management of bone metastasis in prostate cancer: an update, Expert Review of Anticancer Therapy, http://dx.doi.org/10.1080/14737140.2016.1241148, Sep. 27, 2016.

Fallowfield et al.., "Patients' preference for administration of endocrine treatments by injection or tablets", results from a study of women with breast cancer, Annals of Oncology vol. 17 No. 2 Feb. 2000, pp. 205-210.

Farwell, et al.., "Total Suppression of Cortisol Excretion by Ketoconazole in the Therapy of the Ectopic Adrenocorncotropic Hormone Syndrome", American Journal of Medicine, filed for case IPR2016-00286, Janssen Exhibit 2065, on Jun. 1988, vol. 84, pp. 1063-1006.

Final Written Decision, United States Patent and Trademark Office Before the Patent Trail and Appeal Board, Case No. IPR2016-01582 U.S. Pat. No. 8,822,438 82, Jan. 17, 2018, 51 pages.

Fizazi et al.., "Abiraterone plus Prednisone in Metastatic, Castration-Sensitive Prostate Cancer", The new england journal of medicine, ,Jul. 2017, vol. 377, No. 4, pp. 352-360.

Fizazi et al.., "Low Incidence of Corticosteroid-associated Adverse Events on long-term Exposure to Low-dose Prednisone Given wilh Abiralerone Acetate to Patients with Metastatic Castration-resislant Prostate Cancer", Eur Urol. Sep. 2016, vol. 70, No. 3, pp. 438-444.

Fossa et al.., "Flutamide versus prednisone in patients with prostate cancer symptomatically progressing after androgen-ablative therapy: a phase III study of the European organization for research and treatment of cancer genitourinary group," Journal of Clinical Oncology, vol. 19( 1 ) 62-71 (2001).

Fossa, et al.., Weekly Docetaxel and Prednisone Versus Prednisolone Alone in Androgen-Independent Prostate Cancer: A Randomized Phase II Study, European Urology, 2007, pp. 1691-1699, vol. 52.

Fourteenth Edition Physicians' Desk Reference to Pharmaceutical Specialties and Biologicals, 1960, PDR, 2 pages.

Friel, Patrick N., et al., Suppression of adrenal function by low-dose prednisone: assessment with 24-hour urinary steroid hormone profiles—A review of five cases , Alternative Medicine Review (2006), 11(1).

G. Sonpavde et al.., Impact of single-agent daily prednisone on outcomes in men wilh metastatic castration-resistant prostate cancer, Prostate Cancer and Prostatic Diseases (2016) 00, pp. 1-5.

Ganger.gov (NIH NCI), "Proslate-specific antigen (PSA) test," http//www.cancer.gov/types/prostate/psa-fact-sheet (accessed Apr. 11, 2017), 8 pages.

Garnick Deposition Blackhard, Letter to Editor, The Journal of Urology. "Official Journal of The American Urological Association, Inc.", file for Case IPR2016-01332, Janssen Exhibit 2011 on Dec. 1991, vol. 146, No. 6, pp. 1621-1622.

Garnick et al.., "Androgen deprivation therapy: the future", Prostate Cancer Principles and Practice, 2006, 19 pages.

Genentech Provides Update on Phase III Study of Avastin in Men With late Stage Prostate Cancer Janssen Exhibit 2081, *Amerigen* vs. *Janssen* filed for Case# IPR2016-00286, Mar. 12, 2010, 3 Pages.

Geoff Cumming, "Inference by eye: reading the overlap of independent confidence intervals", Statistics in Medicine, vol. 28, 2009, pp. 205-220.

Gerber, et al.., Prostate Specific Antigen for Assessing Response to Ketoconazole and Prednisone in Patients with Hormone Refractory Metastatic Prostate Cancer, The Journal of Urology, 1990, pp. 1177-1179, vol. 1444, No. 5.

Ghatana et al... "Effect of Single-agent Daily Prednisone on Outcomes and Toxicities in Metastatic Castration-resistant Prostate Cancer: Pooled Analysis of Prospective Studies", Clinical Genitourinary Cancer, vol. 16, No. 2, Apr. 2018, pp. e277-e287.

Gignac et al., "Castration Resistant, Taxane Naive Metastatic Prostate Cancer: Current Clinical Approaches and Future Directions," J. Urology, vol. 178:S30-S35 (2007).

Gill et al.., "Efficacy of Eplerenone in the Management of Mineralocorticoid Excess In Men With Metastatic Castration-resistant Prostate Cancer Treated With Abiraterone Without Prednisone", Clinical Genitourinary Cancer; vol. 15, No. 4, Aug. 2017, pp. e599-e602.

Gleave et al., "Use of antisense oligonucleotides targeting the cytoprotective gene, clusterin, to enhance androgen • and chemosensitivity in prostate cancer", World J Urol. Feb. 2005, vol. 23, No. 1, pp. 38-46.

Gordon Williams et al., "Objective Responses to Ketoconazole Therapy in Patients with Relapsed Progressive Prostatic Cancer" British Journal of Urology vol. 58, pp. 45-51 (1986).

Gras Jordi: "Niraparib hydrochloride. Poly [ADP-ribose] polymerase (PARP) inhibitor, Oncolytic" , Drugs of the Future, vol. 38, No. 10, Oct. 1, 2013 (Oct. 1, 2013), pp. 679-685, XP009195509, Prous Science, ES ISSN: 0377-8282.

Grinspoon and Biller, "Clinical Review 62 Laboratory Assessment of Adrenal Insufficiency", Journal of Clinical Endocrinology and Metabolism, Filed for Case IPR2016-00286, Janssen Exhibit 2052, on 1994, vol. 79. No. 4, pp. 923-931.

Grove, M. et al., "Bioavailability of Seocalcitol i: Relating Solubility in Biorelevant Media with Oral Bioavalability in Rats-Effect of Medium and Long Chain Ttiglycerides", 94(8) J. Pharm. Sci. No. 1830-1838 (2005).

H.I. Scher et al.., Design and End Points of Clinical Trials for Patients with Progressive Prostate Cancer and Castrate Levels of Testosterone: Recommendations of the Prostate cancer Clinical Trials Working Group, Journal of Clinical Oncology, vol. 26, No. 7, at 1148-1159 (Mar. 1, 2008).

Hadaschik et al.., "Novel targets and approaches in advanced prostate cancer", Current Opinion in Urology 2007, vol. 17: pp. 182-187.

Haidar et al., "Effects of novel 17alpha-hydroxylase/C17, 20-lyase (P450 17, CYP 17) inhibitors on androgen biosynthesis in vitro and in vivo", Journal of Steroid Biochemistry & Molecular Biology, Apr. 2003, vol. 84, No. 5, pp. 555-562.

Haidar et al.., "Novel steroidal pynmidyl inhibitors of P450 17 (17alpha-hydroxyiase/C17-20-lyase)," Arch. Phann. Pharm. Med. Chern., vol. 334:373-374 (2001).

Hakki et al., CYP17- and CYP11B-dependent steroid hydroxylases as drug development targets, Elsevier. 2006, pp. 27-52, vol. 11.

Hansen. C. M. et al.., "Seocalcllol (EB 1089): A Vitamin D. Analogue of Anti-Cancer Potential. Background, Design, Synthesis,. Pre-Clinical and Clinical Evaluation", 6 Current Phannaceutical Design, 803-828 (2000).

Harris, et al.., Low Dose Ketoconazole vvith Replacement Doses of Hydrocortisone in Patients with Progressive Androgen Independent Prostate Cancer, The Journal of Urology, 2002, pp. 542-545, vol. 168.

Harrison's 15th Edition Principles of Internal Medicine, Braunwald Fauci Kasper Hauser Longo Jameson, N Engl J. Med. 341: 156, 1999.

Hartmann et al.., "Synthesis and evaluation of novel steroidal oxime inhibitors of P450 17 (17alpha-hydroxylase/Cm17-20-lyase) and 5alpha-redudase types 1 and 2," J. Med. Chem., vol. 43:4266-4277 (2000).

Harzstark et al.., "Therapies in Development for Castrate-Resistant Prostate Cancer," Expert Rev. Anticancer Ther.; vol. 8(2):259-268 (2008).

Yano, A., et al.., "Glucocorticoids Suppress Tumor Lymphangiogenesis of Prostate Cancer Cells", Clin Cancer Res (2006), vol. 12, pp. 6012-6017.

Yap et al.., "Abiraterone acetate, an oral irreversible inhibitor of CYP450C17, administered to castration refractory prostate cancer patients is safe, suppresses androgen and steroid precursor levels, and has a high degree of durable antitumor activity," J Urology, vol. 177(4 )p. 199 (2007).

Yap et al.., "Targeting CYP17; Established and Novel Approaches in Prostate Cancer" Current Opinion in Pharmacology (Jul. 28, 2008), vol. 8:449-457 (2008).

Z. Zaferiou et al... Managing Metastatic Castration-Resistant Prostate Cancer in the Pre-chemotherapy Setting: A Changing Approach in the Era of New Targeted Agents, Drugs, 76:421-430, Feb. 12, 2016.

(56) References Cited

OTHER PUBLICATIONS

Zafeiris Zaferiou et al.. in Balaji, Chapter 9, Abiraterone for the Treatment of mCRPC, *Amerigen v. Janssen*, Case# IPR2016-00286, pp. 125-155.

Zhang et al., Targeting the MYCN-PARP-DNA Damage Response Pathway in Neuroendocrine Prostate Cancer, Clin Cancer Res 24: 696, 2017.

Zhang et al. parp inhibitor treatment of neuroendocrine prostate cancer, Clin Cancer Res 24: 696, 2017.

Zhang et al., "Help-seeking behavior for erectile dysfunction: a clinic-based survey in China," Asian J Androl, 2014, vol. 16, Issue 1, pp. 131-135.

Zhang, "Poly(ADP-ribos) polymerase inhibitor: an evolving paradigm in the treatment of prostate cancer", Asian J. of Andrology, vol. 16, pp. 401-406, 2014.

Zhou etal , Asian Pacific Journal of Cancer Prevention, 2014; 15:1313-1320.

Zoladex (Registered) 10.8 mg 3-Month (goserelin acetate implant), AstraZeneca (2004) package insert.

Zoladex (Registered) 3.6 mg (goserelin acetate implant), AstraZeneca (2004), package Insert.

Zytiga Brochure, Putting Prednisone in Perspective, "Prednisone reduces the incidence and severity of mineralocorticoid-related adverse reactions associated with Zytiga(Registered)", Janssen Biotech, Inc. Mar. 15, 2015.

Zytiga Label, May 20, 2015, Zytiga(Registered) (abiraterone acetate) Tablets For Oral Administration Initial U.S. Approval: 2011, May 2015, Mylan Pharms. Inc., Exhibit 1065, 30 pages.

Zytiga Presentation—Key Clinical Findings for Patients with mCRPC who have progressed on Androgen Deprivation Therapy, 2016, pp. 1-66.

Zytiga Promotional Brochure—A comparison of The Mechanisms of Action of Select Prostate Cancer Treatments, 2012, pp. 1-12.

Zytiga Promotional Brochure—for patients with mCRPC who received prior Chemotherapy containing Docetaxel, 2012, pp. 1-2.

Zytiga Promotional Brochure—in Men with mCRPC—Mechanism of Action, 2014, pp. 1-2.

Zytiga Promotional Brochure—Prednisone reduces the incidence and severity of mineralocorticoid-related adverse reactions with Zytiga, 2011, 1 page.

Zytiga Promotional Brochure—Zytiga (abiraterone acetate)—Introducing a New Option for Patients with mCRPC before Chemotherapy, 2012, pp. 1-103.

Zytiga Promotional Brochure-Ztiga abiraterone acetate—an Oral Androgen Biosynthesis Inhibitor, 2011, 1 page.

Zytiga Usage-prednisone information Janssen Exhibit 2095, *Amerigen vs. Janssen* filed for Case# IPR2016-00286, 2016.

Zytiga Usage-total promotional spend Janssen Exhibit 2096 *Amerigen vs. Janssen* filed for Case# IPR2016-00286, 2016, 3 Pgaes.

Zytiga Website, About Zytiga(Registered) (abiraterone acetate), "Prescribed Oral Medicalion for Metastatic Castration-Resistant Prostate Cancer", https:/www.zytiga,cornichoosing-zytiga/results-of-zytiga (accessed Apr. 3, 2017), 10 pages.

Zytiga WebsiteHow Zytiga(Registered) (abiraterone acetate) Works, "Zytiga(Registered) Inhibits Androgen Production at 3 Sources-Including the Tumor Itself" https://www.zytiga.com/print/about-zytiga/how-zytliga-works (accessed Jun. 28, 2016).

Zytiga, "Highlights of Alimta prescribing information," 2008, pp. 20.

Zytiga, "Orange Book: Approved Drug Products with Therapeutic Equivalence Evaluations", Amerigen 1035, Sep. 24, 2015, 2 pages.

Zytiga (Trademark) (abiraterone acetate) Tablets For Oral Administration Initial U.S. Approval Issued Apr. 2011. *Wockhardt vs.Janssen*, Flied for Case IPR2016-01582, Janssen Exhibit 2168, 22 pages.

Potter et al.., "Highly potent inhibitors of human cytochrome P-450 (17alpha)," Poster presented at the third drug discoveiy and development symposium, San Diego, California (1993).

Potter et al.., "Novel Steroidal Inhibitors of Human Cytochrome P4501711 (17alpha-Hydroxylase-C17.20-lyase): Potential Agents for the Treatment of Prostatic Cancer," J. Med. Chem, vol. 38:2463-2471 (1995).

Prednisone Side Effects from http://www.drugs.com/sfx/prednisone-side-effects.html?printable=1, (Jul. 8, 2010).

PredniSONE Tablets USP, 1 mg, 2.5 mg, 5 mg, 10 mg, 20 mg and 50 mg, PredniSONE Oral Solubon USP, 5 mg per 5 mL and PredniSONE Intensol (Trademark) Oral Solution (Concentrate), 5 mg per mL, Revised Nov. 2012, 18 pages.

Prelone, Physician's Desk Reference, 54th edition 1959-1960 (2000).

Prostate Cancer End Points Workshop Jun. 21-22, 2004, Bethesda Marriott—Bethesda MD, 66 pages.

Prostate Cancer Principles and Practice, Taylor & Francis (2006) Chapter 93.

Public Citizen Press Room Release—"Antifunal Treatment Should Be Taken Off the Market, Public Citizen Tells FDAD," Filed for Case IPR2016-00286, Janssen Exhibit 2019, on Feb. 24, 2015, 1 page.

R. J. Auchus et al: "Use of Prednisone With Abiraterone Acetate in Metastatic Castration-Resistant Prostate Cancer", The Oncologist, vol. 19, No. 12, Oct. 31, 2014 (Oct. 31, 2014), pp. 1231-1240.

R. Venkitararnan et al.., A Randomised Phase 2 Trial of Dexamethasone Versus Prednisolone in Castration-resistant Prostate Cancer, fairopean Urology, 67, pp. 673-679 (2015).

Raghavan et al., "Prostate Cancer: Moving Forward by Reinventing the Wheel . . . But This Time it is Round." J. Clin. Oncol, Val. 26(28):4535-4536 (2008).

Ramiah et al.. Clinical Endpoints for Drug Development in Prostate Cancer: Current Opinion in Urology, vol. 18:303-308 (2008).

Randy Osborne, "Historic' and 'practice-changing' Zytiga delivers in prostate cancer at ASCO", 2017, 2 pages.

Raritan, NJ, "Janssen Enters Worldwide Collaboration and License Agreement with Tesaro, Inc., for Niraparib in Prostate Cancer", Apr. 6, 2016, pp. 2.

Reid et al.., "CYP17 Inhibition as a Hormonal Strategy for Prostate Cancer," Nature Clin. Prac. Urology, vol. 5(11):610-620 (2008).

Reid et al.., "Inhibition of Androgen Synthesis Results in a High Response Rate in Castration Refractory Prostate Cancer (CRPC)," Annals of Oncol. vol. 18 (Supp. 9): abstract No. 50PD: 173-74 (2007).

Reid et al.., "Selective CYP17 Inhibition with Abiraterone Acetate (AA) Results in a High Response Rate (RR) in Castration-Resistant Prostate Cancer (CRPC) Confirming the Continued Importance of Targeting Androgen Receptor (AR) Signaling," ASCO 2008 Genitourinary Cancers Symposium, abstract No. 50 (2008).

Reid et al.., "Significant and Sustained Antitumor Activity in Post-Docetaxel, Castration-Resistant Prostate Cancer With the CYP17 Inhibitor Abirnterone Acetate," J. Clin. Oncol., vol. 28:(9), pp. 1489-1495 (2010).

Reid, A., et al.., "Annals of Oncology", Educational and Abstract Book of the ESMO Conference Lugano (ECLU), (2007), 18(Supplement 9), ix173-ix174. Abstract 50PD.

Remington—The Science and Practice of Pharmacy, 20th Edition, filed for Case IPR2016-01582, Janssen Exhibit 2026. on 2000, pp. 1363-1370.

Report to the Nation on Prnstale Cancer 2004. Proslate Cancer Foundation.

Richard d. Auchus, "Steroid 17-hydroxylase and 17,20-lyase deficiencies, genetic and pharmacologic", Journal of Steroid Biochemistry & Molecular Biology, 2017, vol. 165, pp. 71-78.

Robert Twycross, "Corticosteroids in Advanced Cancer".filed for Case# IPR2016-00286, Vot 305, pp. 969-970, Oct. 24, 1992.

Ross et al., "Hormone Refractory Prostate Cancer: Choosing the Appropriate Treatment Option," Oncology, vol. 21(2):185-193 (2007).

Rowlands et al.., Esters of 3-Pyridylacetic Acid that Combine Potent Inhibition of 17alpha- Hydroxylase/C17.20-lyase (Cytochrome P45017alpha) with Resistance to Esterase Hydrolysis, J. Med. Chem., vol. 38:4191-4197 (1995).

Ruben H Munoz, Akin Gump Strauss H, t.\UER & Feld LLP, "Zytiga IPR", Mailed for Cast>.# IPR2016-00286, Jun. 29, 2016, 1 page.

(56) References Cited

OTHER PUBLICATIONS

Rumohr et al.., "Current Chemotherapeutic approaches for androgen-independent prostate cancer", Current Opinion in Investigational Drug, Filed for Case IPR2016-01332. Janssen Exhibit 2027, on 2006, vol. 7. No. 6, pp. 529-533.
Runge, Marschall S., et al.., Principles of Molecular Medicine; Second edition; (2006) Humana Press Inc. ISBN: •1-58829-202-9. pp. 365-376 and 482-484.
Ryan et al. , "Impad of prior ketoconazole therapy on response proportion to abiraterone acetate, a 17-alpha hydroxy lase C17.20-lyase inhibitor in castration resistant prostate cancer (CRPC)," J. Clin. Oncol. (Meeting abstracts), vol. 26 (May 20 Supplement), abstract No. 5018 (2008).
Ryan et al.., "Abiraterone Acetare Plus Prednisone in Chemotherapy (Chemo)-Naive castration Resistant Prostate Cancer (CPRC) Patients Not Exposed to Ketoconazole: Results of a Multi-Center Phase II Study," 2009 Genitourinary cancers Symposium (Feb. 26-28, 2009). abstract Submission (2008).
Ryan et al.., "Effect of Concornitant Food Intake on Pharmacokinetics of Abiraterone Acetate, a 17 alpha Hydroxylase C17,20-Lyase Inhibitor in Castration-Resistant Prostate Cancer (CRPC)," Molecular Cancer Therapeutics (Dec. 2007), vol. 6(12):3527s, 2007 AACR•NCI-EORTC International Conference, Poster Session C, abstract No. C2 (2007).
Ryan et al.., "Phase I Evaluation of Abiraterone Acetate (CB7630), a 17 alpha hydroxylase C17,20-Lyase Inhibitor as Secondary Hormonal Therapy in Castration Resistant Prostate Cancer (CRPC)," poster (undated).
Ryan et al.., "Phase II Study of Abiraterone In Chemotherapy-Naive Metastatic Castration-Resistant Prostate Cancer Displaying Bone Flare Disocordant with Serologic Response", Clinical Cancer Research, 2011, Filed for Case IPR2016-00286, Janssen Exhibit 2017, vol. 17, No. 14, pp. 4854-4861.
Ryan et al.., "Phase I Evaluation of Abiraterone Acetate (CB7630), a 17 alpha hydroxy lase C17,20-Lyase Inhibitor in Androgen-Independent Prostate Cancer (AIPG)." ASCO 2007 Prostate Cancer Symposium, abstract No. 278 (2007).
Ryan et al.., "Phase I Evaluation of Abiraterone Acetate (CB7630), a 17 alpha hydroxylase C17,20-Lyase Inhibitor in Androgen-Independent Prostate Cancer (AIPC)." J. Clin. Oncel.. vol. 25 (18S):250s, ASCO Annual Meeting Proceedings Part I, abstract No. 5064 (2007).
Ryan et al.., "Prostate Specific Antigen Only Androgen Independent Prostate Cancer: Natural History, Challenges in Management and Clinical Trial Design." J, Urology, vol. 178:S25-S29 (2007).
Ryan, "Secondary Hormonal Manipulations in Prostate Cancer," Hematology/Oncology Clinics of North America, vol. 20(4).925-934 (2006).
Rydzewska et al., "Adding Abiraterone to Androgen Deprivation Therapy in Men with Metastatic Hormone-sensitive Prostate Cancer: A Systematic Review and Meta-analysis," European Journal of Cancer, vol. 84, 2017, pp. 88-101.
S, Halabi et al.., Prostate-Specific Antigen Changes As Surrogate for Overall Survival in Men With Metastatic Castration-Resistant Prostate Cancer Treated With Second-Line Chemotherapy, Journal of Clinical Oncology, vol. 31, No. 31, pp. 3944-3950 (Nov. 1, 2013).
S, Wilkinson, S. and G, Chodak., "An Evaluation of Intermediate-Dose Ketoconazole in Hormone Refractory Prostate Cancer," European Urology, vol. 45, pp. 581-585, Nov. 26, 2004.
S. M. Withelm et al.., BAY 43-9006 Exhibits Broad Spectrum Oral Arttitumor Adivity and Targets the RAF/MEKIERK Pathway and Receptor Tyrosine Kinases Involved in Tumor Progression and Angiogenesis, Cancer Research,filed for Case# IPR2016-00286, vol. 64, pp. 7099-7109, (Oct. 1, 2004).
S. Oudard et al.., Prostate-Specific Antigen Doubling Time Before Onset of Chemotherapy as a Predictor of Survival for Hormone-Refractory Prostate Cancer Patients, Annals of Oncology vol. 18, pp. 1828-1833, (Nov. 2007).
S. Udhane et al.., Specificity of Anti-Prostate Cancer CYP17A1 Inhibitors on Androgen Biosynthesis, Biochemical and Biophysical Research Communications, filed for Case# IPR2016-00286, vol. 477, pp. 1005-1010, (Elsevier 2016).
Sabroe, T.P. et al., "An Efficient Synthesis of a Key Intermediate for the Biologically Active Vitamin D Analogue. Seocalcitol", Organic Process Research & Dev. vol. 8(1): 133-35 (2004).
Sahu, B., et al., "FoxA1 Specifies Unique Androgen and Glucocortboid Receptor Binding Events in Prostate Cancer Cells" Cancer Research (2013), vol. 73, pp. 1570-1580.
Sandhu et al. "Phase I Study of Poly(ADP)-Ribose Polymerase (PARP) Inhibitor MK-4827(MK) with Antitumour Activity in Sporadic Castration Resistant Prostate Cancer (CRPC)", Asia-Pac J. Clin. Oncol., vol. 8(Suppl. 1), pp. 29-34, 2012 (Abstract 112).
Sandhu et al., "Poly (ADP-ribose) polymerase (PARP) inhibitors for the treatment of advanced germline BRCA2 mutant prostate cancer", Annals of Oncology, 2013, vol. 24, Issue 5, p. 1416-1418.
Sandhu et al., "The poly(ADP-ribose) polymerase inhibitor niraparib (MK4827) in BRCA mutation carriers and patients with sporadic cancer: a phase 1 dose-escalation trial", Lancet Oncol, vol. 14(9), 2013 , pp. 882-892.
Sartor et al.., "Combination therapy: Abiraterone prolongs survival in metastatic prostate cancer". Nature Reviews Cunical Oncology, Aug. 2, 2011, vol. 8, No. 9, pp. 515-516.
Sartor et al.., "Novel Therapeutic Strategies for Metastatic Prostate Cancer in the Post-Docetaxel Setting", Academia-Pharma Intersect Genitourinary Cancer: Prostate, The Oncologist, Nov. 2, 2011. vol. 16, pp. 1487-1497.
Mulcahy, Phase 3 Trial of Immuriotherapy for Metastatic Prostate Cancer Terminated Janssen Exhibit 2082 *Amerigen* vs. *Janssen* for Case#. IPR2016v0028-6, Oct. 17, 2008, 2 Pages.
Murai et al, parp inhibitor resistance mediated by SLFN11 inactivation; Oncotarget 7;76534, 2016.
Murai, et al., "Differential trapping of PARP1 and PARP2 by clinical PARP inhibitors", National Institute of Health, Cancer Res. Nov. 1, 2012; 72(21): 5588-5599.
Murphy W.J. JL Orcutt & P.C. Remus (2012) Patent Valuation: Improving Decision Making through Analysis Hoboken NJ: Wiley.
N. Rornero-Laordenet al., Prospective Evaluation of the Response to Prednisorie-Dexamethasone Switch in Castration-Resistant Prostate Cancer Patients Treated with abiraterone pre-and post-docelaxel, Journal of Clinical Oncology vol. 34, Nov. 14, 2016.
Nakabayashi, M., et al.. "Response to Low-Dose Ketoconazole and Subsequent Dose Escalation to High-Dose Ketoconazole in Patients with Androgen-Independent Prostate Cancer", Amer Cane Soc., 107(5), (2006) pp. 975-981.
National Cancer Institute-seer Stat Fact Sheets: Prostate Cancer Janssen Exihibit 2089, *Amerigen* vs. *Janssen* filed for case # PR2016-00286, Oct. 3, 2016, pp. 1-11.
NCCN Practice Gudcehnes in Oncology. V. Jan. 2005, Prostate Cancer, 41 pages.
NCT01576172, "Abiraterone Acetate and Prednisone With or Without Beliparib in Treating Patients With Metastatic Castration-Resistant Prostate Cancer", ClinicalTrials.gov, Apr. 12, 2012.
NCT01715285 Clinicaltrials.gov, History of Changes for Study: NCT01715285 A Study of Abiraterone Acetate Plus Low-Dose Prednisone Plus Androgen Deprivation Therapy (ADT) Versus ADT Alone in Newly Diagnosed Participants With High-Risk, Metastatic Hormone-Naive Prostate Cancer (mHNPC), Sep. 19, 2019, 13 pages.
NCT01867710 Clinicaltrials gov, "A Randomized Phase 2 Study Evaluating Abiraterone Acetate With Defferent Steroid Ragimens for Preventing Symptoms Associated With Mineralocorticoid Excess in Asymptomatic, Chemotherapy-native and Metastatic Castration-resistant Prostate Cancer (mCRPC) Patients" file for Case IPR2016-00286, Amerigen Exhibit 1187, on Jan. 14, 2017, 4 pages.
NCT02500901, "Enzalutamide and Niraparib in the Treatment of Metastatic Castrate-Resistant Prostate Cancer (CRPC)", ClinicalTrials.gov., Jul. 17, 2015, downloaded on Sep. 29, 2017 from "clinicaltrials.gov/ct2/show/NCT0200901", 7 pages.
New Treatment for Prostate Cancer Under Development May 22, 1996 Wed for Case#. IPR2016-01582.
Newell et al. The Cancer Research UK experience of pre-clinical toxicology studies to support early clinical trials with novel cancer therapies, Elsevier, 2004, pp. 899-906, vol. 40.

(56) References Cited

OTHER PUBLICATIONS

Nimalasena et al,. "Paraneoplastic Cushing's Syndrome in Prostate Cancer: A Difficult Management Problem," BJU International, vol. 101:424-427 (2007).

Nishimura, Kazuo, et al. Potential Mechanism for the Effects of Dexamethasone on Growth of Androgen-Independent Prostate Cancer, Journal of the Naitonal Cancer Institute, 2001, pp. 1739-1746, vol. 93.

Nishiyama, et al.., Hormone/Antihormone Withdrawal and Oexamethasone, for Hormone-Refractoty Prostate Cancer, international Journal of Urology, 10, 1997, vol. 5, 44-47.

Nnane et al.., Inhibition of Androgen Synthesis in Human Testicular and Prostatic Microsomes and in Male Rata by Novel Steroidal Compounds, Endocrinology, 1999, pp. 2891-2897. vol. 140 No. 6.

O'Donnell et al., "Hormonal impact of the 17 (Alpha)-hydroxylase/C 17,20-lyase inhibitor abiraterone acetate (CB7 630) in patients with prostate cancer" British Journal of Cancer, 2004, vol. 90, No. 12, pp. 2317-2325.

Oelkers W. et al., Dose-response relationships between plasma adrenocorticotropin (ACTH), cortisol, aldosterone, and 18-hydroxycorticosterone after injection of ACTH-(1-39) of human corticotropin-releasing honmone in man, Journal of Clinical Endocrinoloty Metabolism, 1988, vol. 66, No. 1, pp. 181-186.

Official Journal of the American Urological Association, "Postate Cancer", Journal Uroloty, vol. 177, No. 4, Apr. 2007, 2 pages.

Offiecial Journal of the American Urological Association, Inc., "The Journal of Urology", vol. 135, No. 4, part 2, filed for Case, IPR2016-00286, Janssen Exhibit 2022 on Apr. 1986, 203A pages, Abstract 397.

Oh W. K., "Secondary hormonal therapies in the treatment of prostate cancer", Urology 60(Supp. 3A): pp. 87-93, (Sep. 2002).

Ohlmann C.H et al., "Androgendeprivation plus Abirateron/Prednison beim metastasierten hormo •• sensitiven Prostatakarzinom", Jul. 21, 2017, pp. 1185-1186.

Oliver Sartor et al.., Effect of Prednisone On Prostate-Specific Antigen in Patients With Hormone-Refractory Prostate Cancer, Urology, 52: 1998, pp. 252-256.

Olmos et al.., "Reply: CHnical Outcome and Prognostic Factors for Patients Treated Within a Phase I Study: The Royal Marsden Hospital Experience," British Journal of Cancer, vol. 99:1365 (2008).

Opar, Alisa, Asco Presenteations Highlight Value of Cancer Biomarkers,: Nature Reviews, vol. 7:547-548 (2008).

Osaba, D., et al., "Health-Related Quality of Life in Men with Metastatic Prostate Cancer Treated with Prednisone alone or Mitoxantrone and Prednisone"< J Clin. Oncol. (1999), 17(6), p. 165-1663.

Ospina et al., "ACTH Stimulation Tests for the Diagnosis of Adrenal Insufficiency: Systernatic Review and Meta-Analysis", The Journal of Clinical Endocrinology & Metabolism Feb. 2016, vol. 101 No. 2 pp. 427-434.

Oudar, Stephane, et al. Actualite dans le cancer de la prostate, Synthese, Bull Cancer 2005; 92 (10), pp. 865-873 (relevance in English abstract).

P. M. Clark et al., "Defining the normal cortisol response to the short Synacthen test", Implications for the investigation of hypothalarnic pituitary disorders, clinical Endocrinology 1998 vol. 49 pp. 287-292.

Palma et al., "ABT-888 Confers Broad In vivo Activity in Combination with Temozolomide in Diverse Tumors", Cancer Therapy: Preclinical, Dec. 1, 2009, pp. 7277-7290.

Paltiel et al., Management of severe hypokalemia inhospitalized patents: a study of quality of care based on computerized databasis, Arch Intren Med. Apr. 23, 2001, vol. 161, No. 8, pp. 1089, 1095.

Papatsoris et al., "Novel Biological Agents for the Treatment of Hormone-Refractory Prostate Cancer (HRPC)", Current Medicinal Chemistry 2007, filed for Case IPR2016-00286, Janssen Exhibit 2010, vol. 12, pp. 277-296.

Papeo et al., "Poly(ADP-ribose) Polymerase Inhibition in Cancer Therapy: Are We Close to Maturity?", Expert Opinion on Therapeutic Patents, Oct. 2009, vol. 19, No. 10, pp. 1377-1400.

Patent Owner Janssen Oncology, Inc., for U.S. Pat. No. 8,822,438, *Mylan* vs. *Janssen*, filed for case , PR2016-01332, Janssen Exhibit 2189, 86 pages.

PCT Internation Search Report for PCT/US2007/018770, published Feb. 28, 2008.

PCT Written Opinion of the International Searching Authority for PCT/US2007/018770, published Feb. 28, 2008.

Peehl et al., "Preclinical activity of Ketoconazole in combination with calcitriol or the vitamin D analogue EB 1089 in prostate cancer cells," J. Urology, vol. 168, pp. 1583-1588 (2002).

Perlmutter et al: "New Directions in Prostate Caner Management Androgen Deprivation Therapy in the Treatment of Advanced Prostate Cancer", Reviews in Urolog, vol. 9, Jan. 2007, pp. S3-S8.

Petrylak et al.., "Docetaxel and Estramwsline Compared with Mltoxantrone and Prednisonefor Advanced Refractory Prostate Cancer", New England Journal of Medicine, file for Gase IPR2016-01582; Janssen Exhibit 2059, on Oct. 7, 2004, vol. 351, No. 15, pp. 1513-1520.

Petrylak, "Future Directions In The Treatment Of Androgern-Independent Prostate Cancer," Urology 65 (Supplement 6A), pp. 8-13 (2005).

Petrylak, D.P., "New Paradigms for Advanced Prostate Cancer", Rev. Urol. (2007), 9, Suppl. 2, S3-S12.

Phillip et al., Targeting PARP in prostate cancer: novelty, pitfalls, and promise. Oncology, vol. 30, No. 5, May 15, 2016 p. 377-377.

PMLiVe Website, "Top 50 Pharmaceutical Products by Global Sales", http:pmlive.pmlive.com/top pharma list/Top 50 pharmaceutical produds by global sales (accessed Jun. 30, 2016), Mylan Pharms. Inc., Exhibit 1055, 3 pages.

Polkinghorn et al, AR signaling regulates DNA repair in prostate cancer; Cancer discovery 3: 1245, 2013.

Posner. G.H. et al.., A non-Calcemic Sulfone Version of the Vitamin D3 Analogue Seocalcitol (E81089): Chemical Synthesis. Bialogical Evaluation and Potency Enhancement of the Anticancer Drug Adriamycio, Bioargaoic & Medicinal Chem. 9: 2365-71 (2001).

Postma, "Treatment of Prostate Cancer", Annals of Oncology, Sep. 2006, vol. 17, Supplement 10, x207-x210.

Potter et al. "A Convenient Large-Scale Synthesis of Abiraterone Acetate [3Beta-acetoxy-17-(3 pylidyl) androsta-5, 16-diene], a Potential New Drug for the Treatment of Prostate Cancer," Organic Preparations and Procedures Intl, vol. 29(1):123-134 (1997).

Potter et al. "Discovery of highly potent and selective enzyme inhibitors with potential for the treatment of prostate cancer; the important dual role of transition metal chemistry in both drug design and synthesis," Poster presented at the SmithKline Beecham Research Symposium, Robinson College, Cambridge. England (1993).

Harzstark et al.., "Novel Therapeutic Strategies in Development for Prostate Cancer," Expert Opin. investig. Drugs, vol. 17(1):13-22 (2008).

Haynes et al.., "Pharmacology of CB759S, a Highly Potent Inhibitor of Cytochrome P450c17." Proceedings American Association for Cancer Research, vol. 35, Eighty-fifth Annual Meeting, abstract No. 2507 (1994).

Hellersledt et al., "The current state of hormonal therapy for prostate cancer", CA A C, ancer Journal for Clinicians, May-Jun. 2002, vol. 52, No. 3, pp. 154-179.

Heremans GF, Moolenaar AJ. van Gelderen HH. Female phenotype In a male child due to 17-alpha-hydroxylase deficiency. Arch Dis Child, file for Gase IPR2016-00286, Amerige11 Exhibit 1167 on 1976, vol. 51. No. 9 pp. 721-723.

Herr and Pfitzenmaier. "Gkicocorticoid use in prostate cancer and other solid tumours: implications for effectiveness o cytotoxic treatment and metastases," The Lancet Oncol, Filed for Case IPR2016-00286, . . . Ianssen Exhibit 2023, 01: May 2006, vol. 7 pp. 425-430.

Highlights of Zytiga Prescribing Information, 2015.

Highlights of Zytiga Prescribing Information, 2018.

Hildesheim, "Prostate cancer pill extends life", Lancastria.net. May 26, 2011, 5 pages.

(56) References Cited

OTHER PUBLICATIONS

Horsham, Pa, Dec. 10, 2012—US. FDA Approves Expanded Zytiga (Registered) Indication For Treatment Of Metastatic Castration-Resistant Prostate Cancer Johnson & Johnson, Services, Inc. 1997-2017. 5 pages.
Hotte and Saad, "Current management of castrate-resistant prostate cancer," Current Onoology—vol. 17, Supplement 2,. S72-S79 2010 filed for Case# IPR2016-00286.
How Zytiga(Registered) (abiraterone acetate) Zytiga (Registered) Inhibits Androgen Production at 3 Sources-Inclucting the Tumor Itself Works, https://www.zytiga.com/print/about-zytiga/how-zytiga-works (accessed 7123/2015).
Hsieh et al., "Novel Concepts in Androgen Receptor Blockade," The Cancer Journal (Jan./Feb. 2008), vol. 14(1):11-14.
Huggins, Charles, et al. Studies on Prostatic Cancer.I. The Effect of Castration. of Estrogen and of Androgen Injection on Serum Phosphatases in Metastatic Carcinoma of the Prostate, Cancer Research, •1941, pp. 293-297, vol. 1.
Huggins, C., et al.. "Studies on Prostatic Cane.er. I. The Effect of Castration, of Estrogen and Androgen Injection on Serum Phosphatases in Metastatic Carcinoma of the Prostate". Cancer Res. 22(4), (1972) pp. 232-240.
Hussain et al., "Co-targeting androgen receptor (AR) and DNA repair: A randomized ETS gene fusion-stratified trial of abiraterone + prednisone (Abi) +/− the PARP1 inhibitor veliparib for metastatic castration-resistant prostate cancer (mCRPC) patients (pts) (NCI9012)—A University of Chicago phase II consortium trial", Journal of Clinical Oncology, vol. 34, No. 15, May 20, 2016.
Hussain, Maha, et al., "Targeting Androgen Receptor and DNA Repair in Metastatic Castration-Resistant Prostate Cancer: Results from NCI9012" Journal of Clinical Oncology, American Society of Clinical Oncology, Apr. 1, 2018, vol. 36, No. 10, pp. 991-1009.
In the United States District Court, for the District of New Jersey, BTG International Limited, Janssen Biotech, Inc., Janssen Oncology, Inc., Janssen Research & Development, LLC, for Case# 15-cv 05909-KM-JBC, "Plaintiffs' Opening Claim Construction Brief" Document# 209 Filed 06130/16 p. 1 of 15.
In the United States District Court, for the District of New Jersey, *BTG International Umited, Janssen Biotech, Inc., Janssen Oncology, Inc., Janssen Research & Development, LLC*, (Plaintiffs) vs. *Actavis Laboratories FL Inc*, Case# 15-cv-05909-KM-JBC, "Plaintiffs' Responsive Claim Construction Brief" Document 220 Filed Aug. 31, 2016 p. 1 of 25.
Information concerning Zytiga (abiraterone acetate) from http://www.kampendium.ch/prod/pnr/1183238lde?Platfonn=Desktop as of Mar. 25, 2014.
INSPRA (eplerenone) tablets, Initial U.S. Approval: 2002, *Wockhardt v. Janssen* filed for Case# IPR2016-01332, Janssen Exhibit 2129, 8 Pages.
International Search Report dated Jul. 13, 2018; International Application No. PCT/US2018/026661.
International Search Report dated Sep. 29, 2017; International Application No. PCT/US2017/044413.
Isaacs et al., Identification of ABR-215050 as lead second generation quinoline-3-carboxamide anti-angiogenic agent for the treatment of prostate cancer, The Prostate. Dec. 2006, vol. 66, No. 16, pp. 1768-1778.
J J. Body, "Low-dose prednisone and increased risk of development of bone metastases", Annals of Oncology, file for Case IPR2016-00286, Janssen Exhibit 2061, on 1996, vol. 7, pp. 643-645.
J. Gonzaalbez et al.., "Establishment of reference values for standard dose short synacthen test (250 microgram). low dose short synacthen test (1 microgram) and insulin tolerance test for assessment of the hypothalamo-pituitary-adrenal axis in normal subjects", Clinical Endocrinology 2000, vol. 53, 199-204.
J. Trachtenberg and A. Pont, The Lancet, Ketoconazole Therapy for Advanced Prostate Ganeer, Aug. 25, 1984, pp. 433-435.
Jakobsen et al.., "Medroxyprogesterone Acetate and Prednisone in Advanced Breast Cancer. A Randomized Trial," Eur. J Cancer Clio. Oncol.. vol. 22:9. pp. 1067-1072 (1986).

Janssen Announces Preliminary Results from Phase 2 GALAHAD Study in Adults with Metastatic Castration-Resistant Prostate Cancer and DNA-Repair Pathway Defects (DRD), Feb. 14, 2019, 8 pages.
Janssen Announces U.S. FDA Breakthrough Therapy Designation Granted for Niraparib for the Treatment of Metastatic Castration-Resistant Prostate Cancer, Oct. 3, 2019, 4 pages.
Janssen Exhibit 2006, *Amerigen v. Janssen* IPR2016-00286, Clinical Cancer Research, A Journal of the American Association for Cancer Research, Letter to lan Judson. RE: "Manuscript# 030579, Hormonal impact of the 17a-hydroxylase/C17, 20-lyase inhibitor abiraterone acetate (CB7630) in patients with prostate cancer", Dated May 12, 2003, 4 pages.
Janssen research & Development, LLC "A Safety and Pharmacokinetics Study of Niraparib Plus an Androgen Receptor-Targeted Therapy in Men With Metastatic Castration-Resistant Prostate Cancer (Bedivere)", ClinicalTrials.gov, Oct. 5, 2016 (Oct. 5, 2016).
Janssen Research & Development. Clinical Study Report Synopsis Protocol JNJ-212082-JPN-201; Phase 2, 2015, 9 pages.
Jarman el al., "The Mechanism of Irreversible Inhibition of Human Cytochrome P45017alpha by Abiraterane, a Potential New Drug for the Treatment of Prostate Cancer:" Annals of Oncol.). vol. 9(SuppL 2): 135, 10th NCL-EORTC Symposium on New Drugs in Cancer Therapy, abstract No. 516 (1998).
Jarman et al., "The 16.17-Double Bond is Needed for Irreversible Inhibition of Human Cytochrome P45017alpha by Abiraterone (17-(3. Pyridyl)androsta-5, 16-dlen-3Beta-ol) and Related Steroidal Inhibitors," J. Med. Chem.. vol. 41:5375-5381 (1998).
Jarman et al.., "Enzyme Inhibitors In Endocrinology," J. Endocrinology, vol. 148 (Suppl.), abstract No. S23 (1996).
Jemal, A., et al., "Cancer Statistics, 2007", CA Cancer J Clin, 57, (2007) pp. 43-66.
Jennifer Craft, "Eplerenone (Inspra), a new aldosterone antagonist for the treatment of systemic hypertension and heart failure", Baylor University Medical Center Proceedings, file for Case IPR2016-00286, Janssen Exhibit 2062, on Apr. 2004, vol. 17, No. 2, pp. 217-220.
Jevtana (Registered) (cabazilaxel) injection, for intravenous use Initial U.S. Approval: 2010, Jevtana Label, Sep. 2016, *Amerigen vs. Janssen* filed for case IPR2016-00286, Amerigeo Exhibit 1149, 25 pages.
Jevtana prescribing information (Sep. 2016), Jevtana(Registered) (cabazitaxel) injection, for intravenoos use Initial U.S. Approval 2010, 25 pages.
Jevtana Website. "Dosing and Administration", http://www.jevtana,com/hcp/dosing/defaultaspx (accessed Jun. 28, 2016), Mylan Pharms, Inc., Exhibit 1049, 4 pages.
Jhun et al., "Gene expression signature of Gleason score is associated with prostate cancer outcomes in a radical prostalectomy cohort", Oncotarget, Jun. 2017, vol. 8, No. 26, pp. 43035-43047.
John S, et al., "Secondary Hormonal Therapy for Advanced Prostate Cancer", The Journal fo Urology, vol. 175, Jan. 2006, pp. 27.34.
Johnson & Johnson Announces Definitive Agreement to Acquire Cougar Biotechnology, Inc,, Access to Late-Stage, First-in-Class Prostate Cancer Treatment Strengthens Presence in Oncology May 21, 2009, pp. 4.
Johnson & Johnson, "Zytiga Approved in the EU for Use in tile Treatment of Metastatic Castration-Resistant Prostate Cancer Before Chemotherapy," Jan. 11, 2013, 4 pages.
Jones et al., "A Poly(ADP-ribose) Polymerase (PARP) Inhibitor for the Treatment of Tumors with Defective Homologous Recombination", J. Med. Chem., Apr. 23, 2015, 58(8), 3302-3314.
Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors", J. Med. Chem. 2009, vol. 52, pp. 7170-7185.
Jubelirer and Hogan, "High Dose Ketoconazole For The Treatment of Hormone Refractory Metastatic Prostate Carcinoma; 16 Cases And Review Of The literature," The Journal of Urology, Filed for Case IPR2016-00286, Janssen Exhibit 2018, on Jul. 1989, vol. 142, No. 1. pp. 89-91.

(56) References Cited

OTHER PUBLICATIONS

Julian Seifter et al.., "Concepts in Medical Physiology", Lippincott Wiluams and Wilkins, *Wockhardt* vs, *Janssen*, Files for Case IPR2016-01582, Janssen Exhibit 2171, 2005, 540-620 pages.

Juliet Richards et al., Interactions of Abiraterone, Eplerenone, and Prednisolone with Wild-type and Mutant Androgen Receptor: A Rationale for Increasing Abiraterone Exposure or Combining with MDV3100, Cancer Res; 72(9) pp. 2176-2182, May 1, 2012.

K, Akakura et al., Possible Mechanism of Dexamethasone Therapy for Prostate Cancer: Suppression of Circulating Level of Inledeukin-6, The Prostate, 56:106•109 (2003).

Continuing Challenge of Hormone-Refractory Prostate Cancer, Declaration ot Oliver Sartor, "Clinical Genitourinary Cancer", filed for case Janssen IPR2016-01582, Janssen Exhibit 2156 on Mar. 2006, pp. 238-239.

Cooper et al.., "Mechanisms of Disease: Biomarkers and rv'lolecular Targets from rvlicroarray Gene Expression Studies in Prostate Cancer," Nature Ctn Practice OncoL, vol. 4('12):677-687 (2007).

Costa-Sanlos, M. et al.. "Two Prevalent CYP17 Mutations and Genotype-Phenotype Correlations in 24 Brazilian Patients with 17-Hyctroxylase Deficiency," J, Clin. Endocrin. & MetaboL vol. (89)1, pp. 49-60, 2004.

Cougar Biotechnology Announces Presentation of Positive CB7630 Clinical Data at AACR-NCI-EORTC International Conference on Molecular Targets and Cancer Therapeutics, News Release, available at: http://www.cougarbiotechnology.com (2007).

Cougar Biotechnology Inc. with the U.S. Securities and Exchange Commission, From 10-QSB, 2013.

Cougar Biotechnology, A Phase ilii Open Label Study of the 17-Hydroxylas-e/ c17-20 lyase Inhibitor, Abiraterone Acetate in Patients with Prostate Cancer Who have Failed Hormone Therapy, Latter to Johann De-Bono, Re: Revised abiraterone protocol, Dec. 6, 2004, 86 pages.

Cougar Biotechnology, Cougar Biotechnology Announces Initiation of Phase I/II Trial for CB7630 (Arbiraterone Acetate), Cougar Biotechnology, Dec. 14, 2004.

Cougar Biotechnology, Cougar Biotechnology Announces Presentation of Positive CB7630 Clinical Data at ESMO Conference, Drugs.com, Jul. 2007.

Cougar Biotechnology, Cougar Biotechnology announces presentation of positive phase I and phase II data at ASCO Prostate Cancer Symposium, Cougar Biotechnology, Feb. 23, 2007.

Cougar Biotechnology, Cougar Technology Announces Presentation of Positive CB7630 Clinical Data at ASCO Annual Meeting, The Free library, Jun. 4, 2007.

Cougar Biotechnology, Inc., Clinical Study Report: COU-AA-001 and COU-AA 001 EXT, Nov. 17, 2010, 7 pages.

Cowen & Company, "Biotechnology Quarterly."Jul. 2, 2012.

Cowen & Company, "Quick Take: Zytiga Gets FDA OK For Use In Pre-Chemo Setting On rPFS Data-Johnson & Johnson."Accessed (Dec. 11, 2012).

Crawford et al.., "Treating Patients with Metastatic Castration Resistant Prostate Cancer", A Comprehensive Review of Available Therapies, The Journal of Urology, vol. 194, Dec. 2015, pp. 1537-1547.

Credit Suisse, "Prostate Cancer—Implications of Zytiga's Pre-Ghemo Approval" Dec. 11, 2012.

Czock, et al.., "Phatmacokinetics and Pharmacodynamics of Systemically Administered Glucocorticolds", Pharmacokinet (2005), 44(1), p. 61-98.

D. Feldman,"Keloconazole and Other Imidazole derivatives as Inhibitiors of steroidogenesis", filed for Case# IPR2016-00286, 1986, vol. 7, No. 4, 12 pages.

D. Lorente et al.., Tumour responses following a steroid switch from prednisone to dexamethasone in castration-resistant prostate cancer patients progressing on abiraterone, British Journal of Cancer, (2014) 111, pp. 2248-2253.

D.E. Rathkopf et al.., "Updated Interim Efficacy Analysis and Long-Term Safety of Abiraterone Acetate in Metastatic Castration-Resistant Prostate Cancer Patients Without Prior Chemotherapy(COU-AA-302)". European Urology, filed for Case# IPR20•16-00286, No. 66, pp. 815-825, 2014.

Dalhoff, KA, "Phasell Study of the Vitamin D Analogue Seocalcitol in Patients with Inoperable Hepatocellular Carcinoma". 89(2) Bntish Journal of Cancer, 252-257 (2003).

Dalia Buffery, "The 2015 Oncology Drug Pipeline: Innovation Drives the Race to Cure Cancer", Am Health Drug Benefits, vol. 8(4), 2015, pp. 216-222.

Daniel C Danila et al.., "Prednisone Therapy in Patients With Doc-etaxel-Treated Castration-Resistant Prostate Cancer", Joumal of Clinical Oncology, vol. 28, No. 9, Mar. 20, 2010. pp. 1496-1501.

Danielenko et al.., "Enhancernent by other compounds of the anti-cancer activity of vitamin D3 and its analogs;" Experimental Cell Research, vol. 298 (2):339-358 (2004).

Danila et al.., "Abiraterone acetate and prednisone in patients (Pts) with progressive metastatic castration resistant prostate cancer (CRPC) after failure of docetaxel-based chemotherapy," J. Clin. Oncol. (Meeting abstracts), vol. 26 (May 20 Supplement), abstract No. 5019 (2008).

Danila et al.., "Preliminary Phase II Results of Abiraterone Acetate in Patients With Castration Resistant Metastafic Prostate Cancer After Failure of Docetaxel-Based Chemotherapy: COU-AA-004," in Innovative Cancer Therapy for Tomorrow: Foundation Symposium XXV; presentatinn (2007).

Danila et al.., "Preliminary Phase II Results of Abiraterone Acetate in Patients with Castration-Resistant Metastatic Prostate Cancer After Failure of Docetaxel-Based Chemotherapy," ASCO 2008 Genitourinary Cancers Symposium, abstract No. 3 (2008).

Danila et al.., Phase II Multicenter Study of Abiraterone Acetate Plus Prednisone Therapy in Patients With Docelaxel-Treated Castration-Resistant Prostate Cancer. Journal of Clinical Oncology, Filed for Case IPR2016-01332, Janssen Exhibit 2016, on Mar. 20, 2010, vol. 28, No. 9, pp. 1496-1501.

Datta et al.., The Journal of Urology, 1997, 158, 175-177.

De Bono et al. Antitumor Activity of Abiraterone Acetate, a CYP17 Inhibitor That Blocks Androgen Synthesis, in Castration-Resistant Prostate Cancer: ASCO 2008 Annual Meeting, Presentation.

De Bono et al.., "Anti-tumor activity of abiraterone acetate (AA), a CYP17 inhibitor of androgen synthesis, in chemotherapy naive and docetaxel pre-treated castration resistant prostate cancer (CRPC)," J. Clin. OncoL (Meeting abstracts),. vol. 26 (May 20 Supplement), abstract No. 5005 (2008).

De Bono et al.., Inhibition of CYP450c17 by abiraterone admir1istered once daily to castrate patients with prostate cancer resistant ta LHRH analogues,. anti-androgens and steriod therapy 1s well tolerated, The institute of Cancer Research, 2007.

de Bono et al... Ablraterone and Increased Survival in Metastatic Prostate Cancer\ New England Journal of fvledidne, filed for case IPR2016-01582, Janssen Exhibit 2159, on May 26, 2011, Established in 1812, vol. 364, No. 21, pp. 1995-2005.

De Coster et al... "P450-Dependenl Enzymes as Targets for Prostate Cancer Therapy," J. Steroid Biochem. Malec.. Biol., vol. 56(1-6):133-143 (1996).

De Coster, et al.., Effects of High-Dose Ketoconazole and Dexamethason on ACTH-Stimulated Adrenal Steriodqienesis in Orchiectomiz:ed Prostatic Cancer Patients, ACTA Endocnnologica (Copenh), ,1987, pp. 265-271, vol. 115.

DeBono et al.., Clinical and endocrine evaluation of abiraterone acetate (AA), a rationally designed small molecule inhibitor of androgen synthesis targeting 17Alfa hydroxy lase (170H)/17,20 lyase in patients with honnone refractory prostate cancer, 2005 Prostate Cancer Symposium, Abstract No. 290.

Declaration of Dr. Gerhardt Attard, 2015, 29 pages.

Deltasone—prednisone tablet Pharmacia and Upjohn and Company, Deltas one (Registered) prednisone tablets, USP. 2007, 13 pages.

DeMario et al.., "Oral Chemotherapy", Rationale and Future Directions, Journal of Clinical Oncology, vol. 16. No. 7, Jul. 1998, pp. 2557-2567.

Dennis L Kasper, et al (Eds.), Harrison's Principles of Iniernal Medicine, 16th Edition (2005), 12 pages.

(56) References Cited

OTHER PUBLICATIONS

Di Cerbo et al.., "Combined 17 alpha-Hydroxylase/17, 20-lyase deficiency caused by Phe93 Cys mutation in the CYP17 gene", The Journal of Clinical Endocrinology & Metabolism 2002, vol. 87, No. 2 pp. 898-905.
Dickstein G et al.., "One microgram is the lowest ACTH dose to cause a maximal cortisol response. There is no diurnal variation of cortisol response to submaximal ACTH stimulation". European Journal of Endocrinology 1997, vol. 137 No. 2 pp. 172-175.
Dickstein G., et al.., "Low' dose ACTH test—A word of caution to the word of caution" when and how to use ii Journal of Clinical Endocrinology and Metabolism 1997, vol. 82 No. 1, 322 pages.
Division of Endocrinology et al.., "Dose-response aspects in the clinical assessment of the hypothalamo pituitary-adrenal axis and the low-dose adrenocorticotropin test", European Journal of Endocrinology, 1996, 135: pp. 27-33.
Dizdar 2015, Is Dexarnethaoone a Better Partner for Abiraternne Than Prednisolone, The Oncologist May 2015 vol. 20, No. 5 e 13.
Donold L. Trump et al.., High-Dose Ketoconazole in Advanced Hormone-Refractory Prostate Cancer: Endocrinologic and Clinical Effects, Journal of Clinicol Oncology, vol. 7, No. Aug. 8, 1989, pp. 1093-1098.
Dorff, TB, Crawford, ED. Management and challenges of corticosteroid therapy in men with metastatic castrate-resistant prostate cancer, Annals of Oncology, 2013. pp. 31-38, vot 24(1).
Dorin et al.., "Diagnosis of Adrenal Insufficiency", Academia and Clinic, Annals of Internal Medicine, Filed for Case IPR2016-00286, Janssen Exhibit 2051, on Aug. 5, 2003, vol. 139, No. 3, pp. 194-204.
Due et al., "In vitro and in vivo models for the evaluation of potent inhibitors of male rat 17 (Alpha)-hydroxylase/C17,20-lyase," Journal of Steroid Biochemistry & Molecular Biology, 2003, Filed for Case IPR2016-01332, Janssen Exhibit 2012, vol. 84 pp. 537-542.
ECOG Perfoimance Status, "Developed by the Eastern Cooperative Oncology Group, Robert L Combs, MD, Group Chair",. *Wockhardt v. Janssen*, Field for Case# IPR2016-01582, Janssen Exhibit 2158, http://ecog-acrin.org/resources/ecog-pertormance-status, Mar. 14, 2017, 2 pages.
Edward G. Bigueri, et al.., "17-Hydroxylation Deficiency in Man", Journal of Clinical Investigation, vol. 45, No. 12. 1966,. 10 pages.
Theodore, "Cancers Genlio-Urinaires," Oncologie, vol. 10:497-500 (2008) (partial English translation enclosed).
Therasse et al.., "New Guidelines to Evaluate the Response to Treatment in Solid Tumors Journal of the National Cancer Instituie", vol. 92, No. 3, Feb. 2, 2000 pp. 205-216.
Thirty Second Edition Physiclans' Desk Reference, 1978, PDR, 6 pages.
Toshihiko Yanase et al.., "Deletion of a phenylalanine in the N-terminal region of human cytochrome P-450(17 alpha) results in partial combined 17 alpha-hydroxylase/17, 20-lyase deficiency" Joumal of Biological Chemistry May 24, 1989, vol. 264 No. 30 p. 18076-18082.
Trelstar (Trademark) Depot 3.75 mg (triptorelin pamoate for injectable suspension), Pharmacia &. Upjohn Company (2001), package insert.
Trelstar(Trademark) LA 11.25 mg (triptorelm pamoate for injectable suspension), Pharmacia & Upjohn Company (2001), package insert.
Trepanier, "Glucocorticoids", Cliniciansbrief.com, Dec. 2005 5 pages.
Trial of Abiraterone Without Exogenous Glucocorticoids in Men With CRPC With Correlative Assessment of Hormone Intermediates, 2013, 10 pages.
Trump et al., "Phase II trial of high-dose, intermittent calcitriol (1,25 dihydroxyvitamin 03) and dexamethasone in androgen-independent prostate cancer," Cancer, vol. 106(10), pp. 2136-2142 (2006).
Truven Commercial and Medicare Data, *Wockhardt vs. Janssen*, Filed for case IPR2016-01332, Janssen Exhibit 2135, 2016, 12 pages.

Tucker et al.., "Reversible Adrenal Insufficiency Induced by Ketoconazole" Janssen Exhibit 2090, *Wockhardt vs. Janssen*, Case# IPR2016-01582, JAMA, vol. 253, No. 16 Apr. 26, 1985, 2 Pages.
Twenty Nineth Edition Physicians' Desk Reference, 1975, PDR, 4 pages.
U,S. Patent. Alan H, Auerbach, et al.., U.S. Pat. No. 8,822,438 B2, "Methods and Compositions for Treating Cancer", flied for Case# 15-cv-05909-KM-JBC, Document# 288-1, filed on Feb. 13, 2017, p. 2 of 13.
U.S. Food and Drug Administration ("FDA"), "FDA Approves New Indication for Taxotere-Prostate Ganeer", FDA News Release dated May 19, 2004, 2 pages.
U.S. Food and Drug Administration FDA New-s Release, "FDA expands Zytiga's use for late-stage prostate cancer", Dec. 10, 2012 http://www.fda.gov/NewsEvents/Newsroom/PressAnnouncements/ucm331492.htm (access Jun. 30, 2016), 2 pages.
U.S. Food and Drug Administration, "FDA News Release", Press Announcements> FDA approves Zytiga for late-stage prostate cancer, Janssen Exhibit 2070, *Amerigen v. Janssen*, for Case# IPR2016-00286, Apr. 28. 2011, 2 Pages.
U.S. Food and Drug Administration, "Orange Book: Approved Drug Products with Therapeutic Equivalence Evaluations" *Wockhardt v. Janssen* IPR2016-00286 Janssen Exhibit 2107 Oct. 3, 2016.
U.S. Food and Drug Administration, FDA Websrte Drugs@FDA—Zytiga, http://www.accessdata.fda.gov/scripts/cder/drugsatfda/index.cfm? fuseaction=Search.DrugDelails (accessed Jun. 28, 2016), Mylan Pharms, Inc., Exhibit 1046, 2 pages.
UBS Investment Research, "Johnson & Johnson—Zytiga Label Extended," Dec. 10, 2012.
UBS Research, "Medivalion—A look at the Growth and Share in Prostate Cancer," Feb. 3, 2014.
Understanding the role of prednisone In combination with ZYTIGA(Registered), (abiraterone acetate), Putting Prednisone in Perspective, 2011, 13 pages.
Understanding Zytiga Users "Urologist Success" Qualitative Research, Janssen Exhibit 2092, *Amerigen vs. Janssen* filed for Case# IPR2016-00286, Jan. 2014.
Veliparib (ABT-888) is a PARP inhibitor being investigated to treat non-small cell hmg cancer, BRCA breast cancer and ovarian cancer, 2019, https://www.abbvie.com/onr- science/pipeline.html.
Venkitaraman, R., et al.., "Efficacy of low-Dose Dexamethasone in Castration-Refractory Prostate Cancer", BJU Int (2008), 101, pp. 1756-1764.
VIADUR(Registerd) (leuprolide acetate implant). Bayer Pharmaceuticals Corporation (2004), package insert.
Vidal et al.., "Reversing Resisiance to Targeted Therapy", vol. 16—Supplement No. 4, 2004, pp. 7-12.
Vijayakumar, S. et al.., "Clinical Trials Involving Vitamin D Analogs in Prostate Cancer", Cancer J. vol. 11(5): 362-73 (2005).
Vink-Van Wijingaarden et al.., "Inhibition of breast cancer cell growth by cornbined treatment with vitamin D3 analogues and tamoxifen," Cancer Research, American Association for Cancer Research, Baltimore, MD:5711-5717, abstract (1994).
Vitamin D Aids Chemotherapy for Advanced Prostate Cancer, http://www.supplementquality.com/efficacy/VitD.prostate chemo. html (2002).
Vitamin D Boosts Cancer Treatment, http://new-s.bbc.co.uk/l/hi/health/2961806.stm (2003).
Vivek K. Arora et al.., Glucocorlicoid Receptor Confers Resistance to Anti-Androgens by Bypassing Androgen Receptor Blockade, Cell, Dec. 5, 2013: 155(6): 1309-1322.
Vogelzang, N.J., Curriculum Vitae, 2010, 15 pages.
W. H.J. Kruit et al.. Effect of combination therapy with aminoglutethimide and hydrocortisnne on prostate-specific antigen response in metastatic prostate cancer refractory to standard endocrine therapy, Anti-Cancer Drugs, 2004, vol. 15, No. 9, pp. 843-847.
Walsh et al.., "Docetaxel Plus Prednisone or Mitoxantrone Plus Prednisone for Advanced Prostate Cancer," J Urology, vol. 173 :2 p. 456 (2005).
Wang, C., et al.., "Hypertension due to 17a-Hydroxylase deficiency", Australian and New Zealand Journal of Medicine (1978), 8(3), p. 295-299.

(56) References Cited

OTHER PUBLICATIONS

Wedbush Quick Note, "Medivation: Zytiga Market Share Decline Accelerates From Last Quarter," Jul. 14, 2015.
Wells Fargo Sewrities, LLC., Equity Research, "Johnson & Johnson," Jun. 29, 2015.
What You Need to Know About Prostate Cancer, NIH Publication No. 12-1576 (2012) Janssen Exhibit 2091 *Amerigen* vs. *Jans-sen* filed for Case# IPR2016-00286.
White, P.C., "Synthesis and Metabolism of Corticosteroids," Principles and Practice of Endoclinology and Metabolism, Ed. Kenneth L Becker, Philadelphia: Lippincott Williams & Wilkins, Janssen Exhibit 2086 *Amerigen* vs. *Janssen* for Case# IPR2016-00286, 2001, Chapter 72, 704-714.
Whitworth, "Mechanism of glucocorticoid-induced hypertension," Kidney International. vol 31:1213-1224 (1987).
Wikipedia, Corticosteriod, undated. website, 2013.
William Blair, "Biotechnology—Zytiga Fourth-Quarter Sales Imply Xtandi Strength," Jan. 22, 2013.
William Blair, Medivation, Inc. "Looking into Recent Weaknesses: Second-Quarter Preview and Breast Cancer Prospect; Lowering Price Target ta $150 on Adjusting Share Count," Jul. 14, 2015.
William D. Figg et al.. "A Randomized Phase II Trial of Ketoconazole Plus Alendronate Versus Ketoconazole Alone in Patients With Androgen Independent Prostate Cancer and Bone Metastases", The Journal of Urology, vol. 173. pp. 790-796, Mar. 2005.
Williams, "Discontinued Drugs in 2007: oncology drugs," Expert Opinion on Investigational Drugs, vol. 17 No. 12: pp. 1791-1816 (2008).
Xiao-Yan Zhao et al.., Glucocorticoids can promote androgen-independent grow1h of prostate cancer cells through a mutated androgen receptor, Nat Med vol. 6 No. 6, Jun. 2000, pp. 703-706.
Xu et al.., Correlation between Prostate-Specific Antigen Kinetics and Overall Survival in Abiraterone Acetate-Treated Castration-Resistant Prostate Cancer Patients, Clinical Cancer Reserch, Jul. 15, 2015, vol. 21, No. 14 pp. 3170-3177.
Xu Yuxia et al., "Clinical Observation of Abriaterone Acetate and Prednison on Patients with Castration resistant Prostate Cancer", Cancer Research on Prevention and Treatment, 2015, vol. 42, No. 4, pp. 382-384.
Yanase T et al.., 17 alpha hydroxylase/17-20-lyase deficiency: from clinical investigation to molecular definition, Endocrine Revews 1991; vol. 12 No. 1 pp. 91-108.
Yano et al.., "Glucocorticoids Suppress Tumor Angiogenesis and In vivo Growth of Prostate Cancer Cells", Clinical Cancer Reserch, May 15, 2006, vol. 12. No. 10, pp. 3003-3009.
Armstrong and Carducci. "New drugs in prostate cancer," Current Opinions Urology, 2006, Filed for Case IPR2016-00286, Janssen Exhibit 2011, vol. 16, pp. 138-145.
Armstrong et al., "New Drug Development in Metastatic Prostate Cancer," Urologic Oncology: Seminars and Original Investigations, vol. 26: 430-437 (2008).
ASCO Cancer Foundation, Poster Session F: Hormone Refractory, ASCO, 2005.
Asim et al., AR signaling and parp inhibition synergize; olaparib inhibited growth of PC3 prostate tumors; Nature comm 8:374; 2017.
Assessment Report for Zytiga (abiraterone) published 2011 by the CHMP of the EMA.
Attard el al., "Antiturnor Activity with CYP17 Blockade Indicates Thai Castration-Resistant Prostate Cancer Frequently Remains Hormone Driven", Cancer Res 2009, vol. 69, No. 12, Jun. 15, 2009, pp. 4937-4940.
Attard el al.. "Prostate Cancer's Day in the Sun." BMJ, vol. 337: a1256 (2008).
Attard et al., "Selective blockade of androgenic steroid synthesis by novel lyase inhibitors as a therapeutic strategy for treating metastatic prostate cancer," BJU International, vol. 96, pp. 1241-1246 (2005).
Attard et al., "Selective Inhibition of CYP17 with Abiralerone Acetate is Well Tolerated and Results in a High Response Rate in Castration-Resistant Prostate Cancer (CRPC)," Molecular Cancer Therapeutics (Dec. 2007), vol. 6(12): 3455s, 2007 AACR-NCI-EORTC International Conference, Poster Session B, abstract No. B73 (2007).
Attard et al.., Activity, toxicity, and effect on steroid precursor levels of abiraterone (A), an oral irreversible inhibitor of CYP17 (17Alfa-hydroxylase/1720, lyase), in castrate men with castration refractory prostate cancer (CRPC): 2007 Prostate Cancer Symposium, Abstract No. 264.
Attard et al.., "Dissecting Prostate Carcinogenesis Through ETS Gene Rearrangement Studies: Implications for Anticancer Drug Development," J. Clin. Pathol, Val. 61:891-896 (2008).
Attard et al.., "Improving lhe Outcome of Patients with Castration-Resistant Prostate Cancer Through Rational Drug Development," British Journal of Cancer, vol. 95:767-774 (2006).
Attard et al.., "Management Strategies for Hormone-Refractory Prostate Cancer", Therapy in Practice, Arn. J. 2006,. vol. 5, No. 3, pp. 163-169.
Attard et al.., "Phase I Clinical Trial of a Selective Inhibitor of CYP17, Ablraterone Acetate, Confirms That Castration-Resistant Prostate Cancer Commonly Remains Honnone Driven." J. Glin. Oncol., vol. 26(26): 4563-4571 (2008).
Attard et al.., "PhaseI study of continuous oral dosing of an irreversible CYP17 inhibitor, abiraterone (A), in castration refractory prostate cancer (CRPC) patients (p) incorporaiing the evaluation of androgens and steroid metabolites in plasma and tumor," .J Clin. Oncology, 2007 ASCO Annual Meeting Proceedings Part I, vol. 25(188), Abstract No. 5063.
Attard et al.., "Predictors of Response and Pharmacodynamic (PD) Endpoints in a Phase I and Pharmacokinetic Study of Abiraterone Acetate (AA) in Castration-Resistant Prostate Cancer (CRPC)," ASCO 2008 Genitourinary Cancers Symposium, abstract No. 214 (2008).
Attard et al.., "Selective Inhibition of CYP17 With Abiraterone Acetate Is Highly Active in the Treatment of Castration-Resistant Prostate Cancer," Journal of Clinical Oncology, Filed for Case IPR2016-002B6, Janssen Exhibit 2015, vol. 27, No. 23, on Aug. 10, 2009, pp. 3742-3748.
Attard et al.., Steroid Hormone Receptors in Prostate Cancer: A Hard Habit to Break?, Cancer Cell, vol. 16, Dec. 8, 2009, pp. 458-462.
Attard et al... Abiratenme, an oral, irreversible CYP450C17 enzyme inhibitor appears In have activity in post-docetaxel castration refractory prostate cancer (CRPC) patients (pts). Annals of Oncology, vol. 18(Supplement 9): ix173-ix174. Abstract No. 51PD (2007).
Attard et al... "Abiraterone Acetate Is Well", Journal of Clinical Oncology, vol. 28, No. 29, Oct. 10, 2010. pp. e560-e561.
Attard G et al.., "Clinical and biochemical consequences of CYP17A1 inhibition with abiraterone given with and without exogenous glucocorticoids in castrate men with dvanced prostate cancer". Journal Of Clinical Endocrinol Metab Feb. 2012, vol. 97 No. 2 pp. 507-516.
Attard, Poster: A randomized trial of abiraterone acetate (AA) administered with 1 of 4 glucocorticoid (GC) regimens in metastatic castration-resistant prostate cancer (mCRPC) patients (pts). J. Clin Oncol 34, 2016 (Suppl 2S: abstr 261). pp. 1-4, Nov. 15, 2016.
Auches et al., "Use of Prednisone With Abiraterone Acetate in Metastatic Castration-Resistant Prostate Cancer", The Oncologist, vol. 19, No. 12, Oct. 31, 2014 (Oct. 31, 2014), pp. 1231-1240.
Auchus et al.., "Human steroid biosynttiesis for the oncologist", NIH Public Access, J Investing Med. Author manuscript: available In PMC May 14, 2013, 22 pages.
Auchus et al.., "Use of Predmsone With Abiraterone Acetate in Metastatic Casiration-Resistant Prostate Cancer", The Oncologist published online Oct. 31, 2014, 10 pages.
Auchus, R.J. "The genetics, pathophysiology, and management of human deficiencies of P450c17," Endocrinology and Metabolism. Clinics of North America. vol. 30, No. 1, pp. 101-119, Mar. 2001.
Auerbach et al., United States Patent and Trademark Office, Before the Patent Trial and Appeal Board, Amerigen Pharmaceuticals Limited and Argentum Pharmaceuticals LLC (Petitioners), Janssen Oncology, Inc. (Patent Owner) for U.S. Pat. No. 8,822,438, "Methods and Compositions for Treating Cancer", filed for Case IPR2016-01582, Amerigen Exhibit 2019 Issued on Sep. 2, 2014, 13 pages.

(56) References Cited

OTHER PUBLICATIONS

Austin and Hux. "A Brief note on overlapping confidence intervals", *Mylan* vs. *Janssen*, Filed for Case IPR2016-01332, "Janssen Exhibit 2184, on 2002, Journal of Vascular Surgery, vol. 36, No. 1, 194-195 pages.
Ayub, M., Inhibition of testicular 17a-hydroxylase and 17,20-tyase but not 3B-hydroixysteroid dehydrogenase-isomerase or 17B-hydroxysteroid oxidoreductase by ketoconazole and other imidazole drugs, Journal of Steroid Biochemistry (1987) 28(5), p. 521-531.
Azad et al.., "Outcomes with Abiraterone Acetate in Metastatic Castration-resistant Prostate Cancer Patients Who Have Poor Performance Status", European Urology, vol. 67, Issue 3, Mar. 2015, pp. 441-447.
B. A. J. Ponder et al.., "Response to aminoglutethimide and cortisone acetate in advanced prostatic cancer", Br. J. Cancer, (1984) 50, pp. 757-763.
Balaji, Managing Metastatic Prostate Cancer in Your Urological Oncology Practice (2016).
Barrie et al.., "17-(3-Pyridyl) Substituted Irreversible Inhibitors of Cytochrome P45017alpha" British J. Cancer, vol. 78(Suppl. 1):34. abstract No. 33 (1998).
Barrie et al.., "Biochemistry and Pharmacokinetics of Potent Non-Steroidal Cytochrome P45017Alpha Inhibitors," J Steroid Biochem. Malec. Biol., vol. 60(5-6):347•351 (1997).
Barrie et al.., "Blochemistryof Potent Cytochrome P45017alpha Inhibitors," British J. Cancer, vol. 75 (Suppl. 1):6, abstract No. 1.7 (1997).
Barrie et al.., "CB7598: A Potent Inhibitor of Steroidal 17alpha-Hydroxylasa/c17,20 Lyase. A Potential New Drug for the Treatment of Prostate Caneer," J. Pharmacy and Pharmacology, vol. 47(128): 1076 (1995).
Barrie et al.., "Highly Potent Inhibitors of Human Cytochrome P-450(17alpha): Activity In Vilro and In Vivo," British J. Cancer (1993), p. 75, BACR/ACP/BOA Annual Meeting, abstract No. 177 (1993).
Barrie et al.., "Inhibitors of Cytochrome P450 17alpha (17alpha-Hydroxylase/C17,20 Lyase)," Endocrine-Related Cancer, vol. 3:25-39 (1996).
Barrie et al.., Pharmacology of Novel Steroidal Inhibitors of Cytochrome P450 17alpha (17alpha-Hydroxylase/C17-20 Lyase; J, Steroid Biocherrt Malec, Biol, vol. 50(5/6)267-273 (1994).
Beardsley et al.., "Systemic Therapy After First-Line Docetaxel in Metastatic castration-Resistant Prostate Cancer," Current Opinion in Supportive and Palliative Gare, vol. 2:161-166 (2008).
Beer et al.., "Weekly high-dose calcitriol and docetaxel in metastatic androgen-independent prostate cancer," .J Clin. Oncology, vol. 21(1) pp. 123-128 (2003).
Bernard P. Schimmer and Keith L. Parker, Andrenocorticotropic Hormone: Adrenocortical Steroids and Their Synthetic Analogs: Inhibitors of the Synthesis and Actions of Adrenocortical Hormones, in Goodman & Gilman's The Pharmacological Basis of Therapeutics, (10th ed. 2001), pp. 1649-1677.
Berry, W. et al.. Phase III Study of Mitoxantrone Plus Low Dose Prednisone Versus low Dose Prednisone Alone in Patients with Asymptomatic Hormone Refractory Prostate Cancer, The Journal of Urology, 2002, pp. 2439-2443, vol. 168.
Biff F. Palmer, "Managin J Hyperkalemia Caused by Inhibitors of the Renin-Angiotensin-Aldosterone System", New England Journal of Medicine, file for Case IPR2016-01332, Janssen Exhibit 2067 on Aug. 5, 2004, vol. 351, No. 6, pp. 585-592.
Biglieri EG et al.., "Herron MA, Brust N. 17-hydroxylation deficiency in man", Journal of Clinical Investigation 1966, vol. 45 No. 12, pp. 1946-1954.
Biophosphonates Fact Sheet. The Paget Foundation http://www.paget.org/information.FactSheet/bisfact/html (Jul. 2006).
Blutt et al.., "A calcitriol analogue, EB 1089, inhibits the growth of LNCaP tumors in nude mice," Cancer Res., vol. 60(4), pp. 779-782 (2000).

Bonnie Gills, "ASCO GU Highlights New Treatment Options for Prostate Cancer", 2016 Highlights from ASH: CLL News, 2015, 5 Pages.
Booth et al.., Oncology's trials, Nature Reviews, vol. 2: Aug. 2003, pp. 609-610.
Borner et al.., "Answering Patients Needs", Oral Alternatives to Intravenous Therapy, The Oncolc-gisl 2001 vol. 6, suppl 4, pp. 12-16.
K. Kobayashi et al., "Mineralocortlcold Insufficiency Due to Suramin Therapy, Cancer", vol. 78, No. 11 (Dec. 1, 1996).
K. Nishimlira el al., Low Doses of Oral Dexamethasone for Hormone-Refractory Prostate Carcinoma, Cancer vol. 89, No. 12, at 2570-2576 (Dec. 15, 2000).
Kaye et al., "New Drug Treatment for Cancer in 2007 Real Progress at Last?" EJC Supplements, vol. 5(4):35, 14th European Cancer Conference, abstract No. 126 (2007).
Kirby M. et al., "Characterising the castration-resistant prostate cancer population: A systematic review", Int'l J. Clinical Practice, vol. 65 No. (11): pp. 1180-1192, (Nov. 2011).
Kissmeyer, A.M. et al.., "The Tissue-specific Distribution of 3H-Seocalcitol (EB 1089) and 3H-calcitriol in Rats", J. of Steroid Bioch. & Mol. Biol. 89-90: 43-47 (2004).
Kluetz P. G. et al., Abiraterone Acetate in Combination with Prednisone for the Treatment of Patients with Metastatic Castration-Resistant Prostate Cancer: U.S. Food and Drug Administration Drug Approval Summary. Clinical Cancer Research, Dec. 15, 2013, vol. 19, No. 24, pp. 6650-6656.
Knol et al.., "The Mis-use of Overlap of Confidence Intervals to Assess Effect Modification", Filed for Case *Wockhardt* v. *Janssen* IPR2016-01332, Janssen Exhibit 2183, on 2011, Eul J. Epidemiol., vol. 26, 253-254 pages.
Koshizuka et al.., "Combined effect of vitamin D3 analogs and paclitaxel on the growth of MCF-7 breast cancer cells in vivo," Breast Cancer Research and Treatment, Springer, New York, NY, vol. 53(2): 113-120 (1999).
Krishnan et al.., "A Glucocorticoid-Responsive Mutant Androgen Receptor Exhibits Unique Ligand Specificity Therapeutic Implications for Androgen-Independent Prostate Cancer," Endocrinology, Filed for Case IPR2016-00286, Janssen Exhibit 2024, on May 2002, vol. 143, No. 5, pp. 1889-1900.
Kuzel et al., "A Phase II Study of Continuous Infusion 5-Fluorouracil in Advanced Hormone Refractory Prostate Cancer", Cancer, file for Case IPR2016-00286, Janssen Exhibit 2054, vol. 72, No. 6, on Sep. 15, 1993, 1965-1968 pages.
Lara and Meyers, "Treatment Options in Androgen-Independent Prostate Cancer" Cancer Investigation, file for Case IPR2016-00286, Janssen Exhibit 2053, vol. 17, No. 2, on 1999, pp. 137-144.
Li et al. AR-induced brcaness and part inhibition in preclinical studies; Sci Signal 10: eaam7479, 2017.
Li et al. targeting parp/cmyb in prostate cancer, with olaparb tested in vibo in Vcap model; Sci Signal 7: ra47; 2014.
Ling et al.., "17-imidazolyl, pyrazolyl, and isoxazolyl androstene derivatives, Novel steroidal inhibitors of human cytochrome C1720-lyase (P45017alpha):" J, Med. Chem., vol. 40:3297-3304 (1997).
Logothetis et al., "Identification of an androgen withdrawal responsive phenotype in castrate resistant prostate cancer (CRPC) patients (pts) treated with abiraterone acetate (AA)," J. Clin. Oncol. (Meeting abstracts), vol. 26 (May 20 Supplement), abstract No. 5017 (2008).
Lupo et al., "Inhibition of poly(ADP-ribosyl)ation in cancer: old and new paradigms revisited", Biochim Biophys Acta, Aug. 2014, vol. 1846, No. 1, pp. 201-215.
Luthy et al.., "Androgenic Activity of Synthetic Progestins and Spironoladone In Androgen-Sensitive Mouse Mammary Carcinoma (Shionogi) Cells in Culture", J. Steroid Biochem, vol. 31, No. 5 Ψ1988. pp. 845-852.
Madan Ravi A et al. Abiraterone Cougar Biotechnolagy IDrugs, Current Drugs Ltd, GB, vol. 9, No. 1, 2006, pp. 49-55.
Mantero et al., "Long-term treatment of mineralocorticoid excess syndromes", Divisions of Endocrinology, Universities of Padua and Ancona, Italy, Steroids, file for Case IPR2016-00286, Janssen Exhibit 2066, on Jan. 1995, vol. 60 pp. 81-86.

(56) References Cited

OTHER PUBLICATIONS

Marc B-Garnick, "Management of Metastatic Carcinoma of the Prostate—Treatment Options and Controversies", in Prostatic Disorders, (David F. Paulson et al. eds., 1989), pp. 354-367.
Maria I., "Male pseudohermaphroditism due to 17 alpha-hydroxylase deficiency", Journal of Clinical Investigation 1970, vol. 49 No. 10 pp. 1930-1941.
Marik PE et al., Recommendations for thedlagnosis and management of corticosteroid insufficiency in critically Ill adult patientsn consensus statements from an international task force by the American College of Critical Care Medicine. Critical Care Medicine 2008, vol. 36, No. 6, pp. 1937-1949.
Marinan Fakih et al., "Glucocorticoids and Treatment of Prostate Cancer: A Precunical and Cunical Review". Urology 60. 2002, pp. 553-561.
Marini et al., "The effect of adjuvant prednisone combined with GMF on patterns of relapse and occurrence of second malignancies in patients wilh breast cancer", Annals of Oncology, file for Case IPR2016-00286, Janssen Exhibit 2060, on 1996, vol. 7, pp. 245-250.
Mark. J. Ratain et al., Statistical and Ethical Issues in the Design and Conduct of Phase Iand II Clinical Trials of New Anticancer Agentsn, Journal of the National Cancer Institute, vol. 85, No. 20, pp. 1637-1649, Oct. 20, 1993.
Martins et al., "A Validated Liquid Chromatographic-Tandem Mass Spectroscopy Method for the Quantification of Abiraterone Acetate and Abiraterone in Human Plasma," J. Chromatography B, vol. 843:262-257 (2006).
Masuda et al., MPromise of vitamin D analogues in the treatment of hyperproliferative conditions, Mol. Cancer Ther., VaL 5(4) pp. 797-808 (2006).
Mateo et al, TOPARP study repoted in NEJM 373:1697-olaparib treatment of prostate cancer patients, 2015.
Mateo et al., "DNA-Repair Defects and Olaparib in Metastatic Prostate Cancer", The New England Journal of Medicine, 2015, vol. 373, No. 18, pp. 1697-1708.
Mayo Clinic "Prednisone and other corticosteroids" for Case# IPR2016-002S6 Janssen Exhibit 2102 Oct. 3, 2016 4 Pages.
Mayo Clinic Website, "Prostate cancer", http://www.mayoclinic.org/diseasesconditions/prostatecancer/basics/definition/con-20029597?p=1 (accessed Jun. 28, 2016), Mylan Pharms. Inc., Exhibit 1051, 11 pages.
McKay et al.., "A phase II trial of abiraterone acetate (AA) without prednisone in castration resistant prostate cancer (CRPC)", Genitourinary (Prostate) Cancer, An American Society of Clinical Oncology Journal, 5 pages.
McPhaul. Michael J., "Mechanisms of Prostate Cancer Progression to Androgen Independence," Best Practice & Research Clinical Endocrinology & Metabolism. vol. 22(2):373-388 (2008).
Medical Dictionary, "Refractory cancer definition of refractory cancer by Medical dictionary" Janssen Exhibit 2103 *Amerigen* vs. *Janssen* filed for Case# IPR2016-00286. Oct. 3, 2016, 1 page.
MedlinePlus, MACTH stimulation test, Available at https://medlineplus.govtency/artide/003696.htm, last visited Sep. 30, 2016, file for Case IPR2016-00286, Janssen Exhibit 2050, 4 pages.
Melby JC et al.., "Comparative studies on adrenal cortical function and cortisol metabolism in healthy adults and in patients with shock due to infection", Journal Clin Invest 1958, vol. 37 No. 12 pp. 1791-1798.
Mendel et al.., "In vivo antltumor activity of SU11248, a novel tyrosine kinase inhibitor targeting vascular endothelial growth factor and plalelet-derived growth factor receptors delermination af a pharmacokinetic/pharmacodynamic relationship", Clinical Cancer Research, Jan. 2003. vol. 9, No. 1. pp. 327-337.
Michaelson et al., "Randomized, Placebo-Controlled, Phase III Trial of Sunitinib Plus Prednisone Versus Prednisone Alone in Progressive, Metastatic, Castration-Resistant Prostate Cancer." Journal of Clinical Oncology, vol. 31. pp. 1-8, (2013).
Michie, C.O., et al., "Final results of the phase I trial of niraparib (MK4827), a poly(ADP)ribose polymerase (PARP) inhibitor incorporating proof of concept biomarker studies and expansion cohorts involving BRCA1/2 mutation carriers, sporadic ovarian, and castration resistant prostate cancer (CRPC)," Journal of Clinical Oncology, vol. 31, No. 15, suppl, May 20, 2013, pp. 2513-2513.
Millikan, et al., "Randomized phase 2 trial of ketoconazole and ketoconazole/doxorubicin in androgen independent prostate cancer" Urologic Oncology, file for Case IPR2016-00286, Janssen Exhibit 2064, on 2001. vol. 6, pp. 111-115.
Milliken et al., EB1089, a vitamin D receptor agonist, reduces proliferation and decreases tumor growth rate in a mouse model of hormone-factuced mammary cancer,M Cancer letters, New York, NY, vol. 229 (2):205-215 (2005).
Mollet et al.., "Highlights on Prostate Cancer from Urological and Oncological Congresses in 2007," European Urolog, Supplements, vol. 7:460-476 (2008).
Moreira et al., "CYP17 Inhibitors for Prostate Cancer Treatment—An Update," Current Medicinal Chemistry), vol. 15:888-899 (2008).
Moreira et al., Synthesis and evaluation of novel 17-indazole androstene derivatives designed as CYP17 inhibitors, Elsevier, 2007, pp. 939-948, vol. 72.
Morgan et al., "Impact of prednisone on toxicities and survival in metastatic castration-resistant prostate cancer: A systematic review and meta-analysis of randomized clinical trials", Critical Reviews in Oncology/Hematology, Jun. 2014, vol. 90, No. 3, pp. 253-261.
Morioka et al., Prostate-Specific Antigen Levels and Prognosis in Patients with Hormone-Refractory Prostate Cancer Treated with Low-Dose Dexarnethasone, Urologia Internationalis vol. 68, at 10-15 (2002).
Mostaghel et al., "Intracrine Androgen Metabolism in Prostate Cancer Progression: Mechanisms of Castration Resistance and Therapeutic Implications," Best Practice & Research Clinical Endocnnology & Metabolism, vol. 22(2) 243-258 (2008).
Mostaghel, E.A., "Abiraterone in the treatment of metastatic castration-resistant prostate cancer", Cancer Management Res. (2014) 6, p. 39-51.
Mostaghel, EA et al. Molecular Pathways Targeting resistance in the androgen receptor for therapeutic benefit, Clin Cnacer Res, Dec. 4, 2013.
Mottet et al.., "Highlights on Prostate Cancer from Urological and Oncological Congresses in 2007," European Urology Supplements, vol. 7:460-476 (2008).
Sartor, et al.., Abiraterone Prolongs Survival in Metastatic Prostate Cancer, Nature Reviews Clinical Oncology, 2011, pp. 515-516, vol. 8.
Saunders et al.., "Inhibition of breast and ovarian carcinoma cell growth by 1,25-dlhydroxyvitamin D3 combined with retinoic acid or dexamethasone," Anti-Cancer Drugs, Rapid Communications of Oxford, vol. 6 (4) 562-569 (1995).
Sawyer et al., "Phase I Study of an Oral Formulation of ZD9331 Administered Daily for 28 Days", Journal of Clinical Oncology, filed for IPR201&.00286, vol. 2•1, No. 9, pp. 1859-1865, May 1, 2003.
Scher et al.., "Bicalutamide for Advanceo Prostate Cancer: The Natural Versus Treated History of Disease", Journal of Clinical Oncology, file for Case IPR2016-00286, Janssen Exhibit 2055, vol. 15, No. 8 on Aug. 1997, pp. 2928-2938.
Scher et al.., "Biology of Progressive, Castration-Resistant Prostate Cancer: Directed Therapies Targeting the Androgen-Receptor Signaling , Axis," J. Clin. Oncol. vol. 23(32):8253-61 (2005).
Scher H.I. et al.., "Increased survival with enzalutamide in prostate cancer after chemotherapy" New Eng. J. Med., vol. 367 No. 13, Sep. 27, 2012, pp. 1187-1197.
Schiewer et al, Dual roles of PARP-1 promote cancer growth and progression, Cancer Discovery 2:1134, 2012.
Scholz, et al, Long-Term Outcome for Men with Androgen Independent Prostate Cancer Treated with Ketoconazole and Hydrocortisone, The Journal of Urology, 2005, pp. 1947-1952. vol. 173.
Schroder, "Progress in Understanding Androgen-Independent Prostate Cancer (APC): A Review of Potential Endocrine-Mediated Mechanisms," Eurovean Urology, vol. 53: 1129-1137 (2008).

(56) References Cited

OTHER PUBLICATIONS

Schulte et al.., The corticolropinreleasing hormone stimulation test a possible aid in the evaluation of patients with adrenal insufficiency Journal of Clinical Endocrinology Metabolism 1984, vol. 58 No. 6, pp. 1064-1067.

Seale and Compton, "Side.-effects of corticosteroid agents", The Medical Journal of Australia vol. 144, No. 3 Feb. 3, 1986 pp. 139-142.

Seocalcitol Versus Placebo in Advanced Hepatocellular Carcinoma LEO Pharma Study http://www.clinicaltrials.gov/c1/show,No. 100051532 (2004).

Sephton, et al.., "Diurnal Cortisol Rhythm as a Predictor of Breast Ganeer Survival", Journal of the National Cancer Institute, vol. 92, No. 12, Jun. 21, 2000, pp. 994-1000.

Seventy One Edition Physicians' Desk Reference, the trusted drug reference for over 70 years, 2017. PDR, 5 pages.

Sharifi et al.., "Secondary Hormonal Therapy for Prostate Cancer: Whal Lies on the Horizon," BJU International, vol. 101:271-74 (2007).

Sills, Irene N., et al.., "17a•hydroxylase deficiency in a genetic rnale and female sibling pair", Int J. GyoaecoL Obstet., (1981), 19, 473:479.

Small et al, "Antiandro.gen Withdrawal Alone or in Combination with Ketoconazole in Androgen-Independent Prostate Cancer Patients: A Phase III Trial (CALGB 9583)" Journal of Clinical Oncology, file for Case IPR2016-01332, Janssen Exhibit 2063, on Mar. 15, 2004, vol. 22, No. 6, pp. 1025-1033.

Small et al.., The Gase fot Socondary Hormaonal Therapies in the Chemotherapy Age, The Journal of Urology, 2006; pp. S66-S71, vol. 176.

Small, E.J., et al.., "Simultaneous Antiaodrogen Withdrawal and Treatment with Ketoconazole and Hydrocortisone in Patients with Advanced Prostate Carcinoma", Amer Cane Soc., 80(9), (1997) pp. 1755-1759.

Smith et al., "Niraparib in patients with metastatic castration-resistant prostate cancer and DNA repair gene defects (GALAHAD): a multicentre, open-label, phase 2 trial", Lancet Oncol., Mar. 2022, 23(3): 362-373.

Sonino et al.., "The Use of Ketoconazole as an Inhibitor of Steroid Production", New England Journal of Medicine, file for Case IPR2016 01332, Janssen Exhibit 2163, on Sep. 24, 1987, vol. 317, No. 13, pp. 812-818.

Sonpavde el al., Impact of single-agent daily prednisone on outcomes in men with metastatic castration-resistant prostate cancerH, Prostate Cancerand Prostatic Diseases, Mar. 2017, vol. 20, No. 1, pp. 67-71.

St. Louis, A Division of J.B. Lippincott, Drug Facts and Comparisons. 1985 Edition, 13 pages.

Stamey et al.., "Prostate-Specific Antigen As A Serum Marker For Adenocarcinoma Of The Prostate," Tile New England journal of Medicine, vol. 317, No. 15, Oct. 8, 1987 pp. 909-916.

Stein, et al.., Randomized Phase 2 Therapeutic Equivalence Study of Abiralerone Acetate Fine Particle Formulation vs. Originator Abiraterone Acetate In Patients With Metastatic Castration Resistant Prostate Cancer: The STAAR Study, Urologic Oncology: Seminars and Original Investigations. 36, 2018, 81.e9-81.e16.

Sternberg, "Systematic Chemotherapy and New Experimental Approaches in the Treatment of Melastalic Prostate Cancer," Annals of Oncol., vol. 19 (Sopp. 7):vii91-vii95 (2008).

Sternberg. "Hormone refractory metastatic prostate cancer", Annals of Oncology, file for Case IPR2016-00286, Janssen Exhibit 2056, on 1992, vol. 3, pp. 331-335.

Storlie. J.A., et al.., "Prostate Specific Antigen Levels and Clinical Response to Low Dose Dexamethasooe for Hormone-Refractory Metastatic Prostate Carcinoma", Cancer (1995) vol. 76, No. 1, p. 96-100.

Strother et al.., "Novel cytotoxic and biological agents for prostate cancer" Where will the money be in 2005?, European Journal of Cancer 2005, filed for Case IPR2.016-00286, Janssen Exhibit 2008. vol. 41, pp. 954-964.

Study NCT03012321 "Abiraterone/Prednisone, Olaparib, or Abiraterone/Prednisone + Olaparib in Patients With Metastatic Castration-Resistant Prostate Cancer With DNA Repair Defects", Clinical Trials, NCT03012321, 2021, pp. 1-13, first posted Jan. 6, 2017.

Summary of Product Characteristics for Zytiga 250mg tablets (Jan. 16, 2014).

Swartz and Dluhy, "Corticosteroids: Clinical Pharmacology and Therapeutic Use", Clinical Pharmacology and Therapeutic, Drugs, file for Case IPR2016-00286, Janssen Exhibit 2068, on 1978, vol. 16, pp. 238-255.

Sweeney et al.., "Chemohomonal Therapy in Metastatic Hormone-Sensitive Prostate Cancer", New England Journal of Medicine, filed for Case Wockhardt vs. Janssen IPR2016-01582, Janssen Exhibit 2163, on Aug. 20, 2015, vol. 373, No. 8, pp. 737-746.

Szmulewitz et al.., "Antiandrogen Therapy in Prostate Cancer," Update on Cancer Therapeutics, vol. 2:119-131 (2007).

T. Saika et al.., Treatment of androgen-independent prostate cancer with dexamethasone: A prospective study in stage D2 patients, International Jaurnal of Urology, 8, pp. 290-294 (2001).

Taichman et al.., The evolving biology and treatment of prostate cance •. The Journal of Clinical Investigation, Sep. 2007, vol. 117, No. 9, 2351-2361.

Takeda et al.., "Inhibitors of the Key Enzymes of Androgen Synthesis: Potential Agents as Targets for Prostate Cancer," Japanese Journal of Clinic ..al Medicine, vol. 58(Suppl.):312-316 (2000); Partial Translation Included (Total pp. 14).

Tamic, R, et al.., "Hormonal Effects of High Dose Medroxyprogesterone Acetate Treatment in Males with Renal or Prostatic Adenocarcinoma", (1988), vol. 22 (1), Abstract.

Tanagho, EA, et al.., "The Leading Single-Volume Resource in Urology" Smith's General Urology, 16th Edition, (2004), Chapter 19, pp. 321-323; Chapter 22, pp. 380-385.

Tannock et al.., Chemotherapy with mitoxantrone plus prednisone or prednisone alone for symptomatic hormone-resistant prostate cancer: a Canadian randomized trial with palliative end points, Journal of Clinical Oncology,. vol. 14,. (6):1756-1764 (1996).

Tannock et al.., "Treatment of metastatic prostatic cancer with low-dose prednisone: evaluation of pain and quality of life as pragmatic indices of response," Journal of Clinical Oncology, vol. 7 590-597 (1989).

Tannock, IF, et al.. Docelaxel plus prednisone or mitoxantrone plus prednisone for advanced prostate cancer, The New England Journal of Medicine, 2004, pp. 1502-1512, vol. 351(15).

Taplin, "Drug Insight Role of the Androgen Receptor in the Development and Progression of Prostate Cancer," Nature Clin. Practice Oncol, vol. 4(4):236-244 (2007).

Taxotere (docetaxel) Injection Concentrate, Aventis Pharmaceuticals Inc. (2005). prescribing information.

Taxotere label, May 2004, Mylan Pharms. Inc. Exhibit 1140.

Taxotere prescribing information (Dec. 2015), Taxotere (docetaxel) Injection Concentrate, Intravenous Infusion (IV). Initial U.S, Approval: 1996, 63 pages.

Taxotere(Registered),"RX Taxotere (Docetaxel) Injecton Concentrate", InformatIn as of May 2004, 35 pages.

Tewari et al.., "Long-Term Survival Probability in Men with Clinically Localized Prostate Cancer Treated Either Conservatively or with Definitive Treatment (Radiotherapy or Radical Prostatedomy)", Urology, Dec. 2006, vol. 68. Issue 6, 1268-1274.

Teyssonneau et al.,"Prostate cancer and PARP inhibitors: progress and challenges", J Hematol Oncol, Mar. 29, 2021, vol. 14 (1):51, 19 Pages.

The Institute of Cancer Research, Abiraterone: a story of scientific innovation and commercial partnership, Making the discoveries that defeat cancer filed for IPR2016-00286 Oct. 3, 2016.

Boudadi et al., "Resistance to Novel Antiandrogen Therapies in Metastatic Castration-Resistant Prostate Cancer", Clin Med Insights Oncol, Feb. 9, 2016, vol. 10, (Suppl 1), pp. 1-9.

Boumpas et al.., "Glucocorticoid Therapy for Immune-mediated Diseases: Basic and Clinical Correlates," Annals of Intemal Medicine, Filed for Case IPR2016-00286, Janssen Exhibit 2021 on Dec. 15, 1993, vol. 119, No. 12 1198-1208.

(56) References Cited

OTHER PUBLICATIONS

Brenner et al. ETS fusion positive prostate tumor models repond to olaparib; Cancer Cell 19 664; 2011.
Brooke et al.., "A novel point mutationin P450c17 (CYP17) causing combined 17alpha-hydroxylase/17,20.lyase deficiency",. The Journal of Clinical Endocrinology & Metabolism, 2006, vol. 91 No. 6 pp. 2428-2431.
Bruno et al., Targeting cytochrome P450 enzymes: A new approach in anti-cancer drug development Elsevier, 2007, pp. 5047-5060, vol. 15.
Bubley et al.., "Eligibility and Response Guidelines for Phase II Clinical Trials in Androgen-Independent Prostate Cancer: Recommendations From the Prostate-Specific Aniigen Working Gmup", Journal of Clinical Oncology, file for Case IPR2016-00286, Janssen Exhibit 2057, on Nov. 1999, vol. 17, No. 11, pp. 3461-3467.
Bundgaard, "Design of Prodrugs", Elsevier, 1985, pp. 1-96.
Burgess and Roth et al.., "Changing Perspectives of the Role of Chemotherapy in Advanced Prostate Cancer," urologic Clinics of North America 2006, filed for case IPR2016-00286, Janssen Exhibit 2007, Vot 33, pp. 227-236.
Burke et al. , "Active-Site Conformation of 17-(3-Pyridyl) Androsta-5, i6-Dien-3Beta--0f, a Potent Inhibitor of the P450 Enzyme C17alpha-Hydroxylase/C17-20 Lyase," Bioorganic & Medicinal Chemistry letters, vol. 5(11):1125-1130 (1995).
C.J. Ryan et al.., "Abiraterone acetate plus preclnisone versus placebo plus prednisone in chemotherapy-naive men with metastatic castration-resistant prostate cancer (COU-AA-302): final overall survival analysis of a randomised, double-blind, placebo-controlledphase 3 study", The Lancet, filed for Case# IPR2016-00286, vol. 16, pp. 152-160, Feb. 2015.
C.J. Ryan et al.., Abiratemne in Metastatic Prostate Cancer without Previous Chemotherapy, The New England Journal of Medicine, 368; 2, pp. 138-148 (Jan. 10, 2013).
C.N. Sternberg et al.., Phase III Trial of Satraplatin, an Oral Platinum plus Prednisone vs. Prednisone alone in Patients with Hormone-Refractory Prostate Cancer, Oncology, 68, pp. 2-9 (2005).
C.W. Ryan et al.., "Dose-Ranging Study of the Safely and Pharmacokinetics of Atrasentan in Patients with Refractory Malignancies", Clinical Cancer Research, filed for IPR2016-00286, vol. 10, pp. 440&-4411, Jul. 1, 2004.
Campbell-Walsh Urology, Ninth Edition, Saunders, vol. 3, Chapters 104 and 105, 2007.
Cancer.0111(ACS), "What are the key statistics abolJt prostate cancer?", http:l/vv\1,w.cancer.org/cancer/prostatecancerfdetaile<iguide/ prostat e-cancer-key-statistics (accessed Jun. 28, 2016), Mylan Pharms. Inc., Exhibit 1041, 2 pages.
Cancer.gov (NIH NCI), "Metastatic cancer," https://www.cancer. gov/types/metastatic-cancer (accessed Oct. 3, 2016), pp. 3 For Case# IPR2016-00286.
Cancer.gov (NIH NCI), Metastatic canceC https://www.cancer.gov/ about-cancer/treatment/drugs/docetaxel (ac<'-essed Oct. 3, 2016), pp. 3 For Case# IPR2016-01332.
Cancer.net (ASCO Patient Website), "Treatment of Metastatic Castration-Resistant Prostate Cancer Sep. 8, 2014", http://www.cancer. net/research-and-advocae:y/asco-care-andtreatment-recommendalions-patients/treatment-metastaticcastration-resistant-prostate-cancer (accessed Jun. 28, 2016), 4 pages.
Cancer.org (ACS), "Hormone therapy for prostate cancer," https:// wwvv.cancer.org/conten/cancer/en/cancer/prostatecancer/ treating/ hormone-therapy•.html (accessed Apr. 10, 2017), 11 pages.
Canger.gov (NIH NCI), "Proslate-specific antigen (PSA) test," http//www.cancer.gov/types/prostate/psa-fact-sheet (accessed Apr. 11, 2017), 8 pages.
Cannell, 100th Annual Meeting of the American Association for Cancer Research, Los Angeles, CA, USA;, http://oncology.thelancel. com, 2007, pp. 471, vol. 8.
Carden et al.., "Crossover Pharmacokinelles (PK) Study to Assess Oral Administration of Abifaterone Acetate Capsule and Tablet Formulations in Fasted and Fed States in Patients with Prostate Ganeer," J. Clin. Oncol. (Meeting abstracts),. vol. 26 (May 20 Supplement), abstract No. 5168 (2008).
Carducci et al.., "A Phase 3 Randomized Controlled Trial of the Efficacy and Safety of Atrasentan in Men With Metastatic Hormone . . . refractory Prostate Cancer," vol. 110, No. 9, Nov. 1, 2007, pp. 1959-1966.
Carducci, MA, HWhat is more exciting? The Activity of Docetaxel in Early Prostate Cancer or the Successful Collaboration between Urologists and Medical Oncologists to complete a study in early Prostate Cancer"?, Journal of Clinical Oncology (2005), vol. 23, Na. 15, pp. 3304-3307.
CB1089, Cougar Biotechnology, Inc., http:/www.cougatbiotechnology. com/eb1089.html, 2006, pp. 1-2.
Cecil Textbook of Medicine, Wyngaarden & Smith 18th edition; Chapter on "Glucocorticosteroid Therapy", Wyngaarden & Smith 18th edition, (1988) p. 128-131.
Centers for Disease Control and Prevention, Prostate Cancer Janssen Exhibit 2100, *Amerigen* vs. *Janssen* filed for Case# IPR2016-00286, 2 Pages.
Chang, Ching-Yi, et al Glucocorticoids Manifest Androgenic Activity in a Cell Derived from a Metastatic Prostate Cancer, Cancer Research, 2001, pp. 8712-8717, vol. 61.
Charles J. Ryan et al.., "Phase I clinical trial of the CYP17 inhibitor abiraterone acetate demonstrating clinical activity in patients with castration-resistant prostate cancer who received prior ketoconazole therapy", Journal of Cunical Oncology Mar. 20, 2010, vol. 28, No. 9, pp. 1481-1488.
Charles L. James et al.., "Antimicrobial Therapy, in Trauma Critical Care", vol. 2, (William C. Wilson et al.. eds., 2007), pp. 927-960.
Charted-ChemoHormonal Therapy versus Androgen Ablation Randomized Trial for Extensive Disease in Prostate Cancer, Declararion of Christopher J. Sweeney, Clinical Advances in Hematology and Oncology, filed for Case IPR2016-01582, Janssen Exhibit 2157, on Aug. 2006, vol. 4, No. 8, pp. 588•590.
Chemicals: Seocalcitol http//ctd.mdibl.org/voc. go:isessionid"126741EAF326D9CE517F360251236091?voc=chem &acc=C078903&queryferms=seocaldtol&qureyType=contains &browser=r (Jul. 17, 2006).
Chen, C.D, et al.., Molecular detemiinants of resistance to antiandrogen therapyx, Nat Med, 10(1), (2004) pp. 33-39.
Cheol Kwak, et al., "Abiraterone acetate and prednisolone for metastatic castration-resistant prostate cancer failing androgen deprivation and docetaxel-based chemotherapy", International Journal of Urology (2014), vol. 21, pp. 1239-1244.
Chi et al.., "A Phase I Pharmacokinetic and Pharmacodynarnic Study of OGX-011, a 2'-Methoxyethyl Antisense Oligonucleotide to Clusterin, in Patients With Localized Prostate Cancer", Journal of the National Cancer Institute, vol. 97, Issue 17, Sep. 7, 2005, pp. 1287-1296.
Chou et al, "Desoxyepothilone B: An efficacious microtubule-targeted antitumor agent with a promising in vivo profile relative to epothilone B", Proc. Natl. Acad. Sci. USA vol. 95, No. 16. Aug. 1998 Pharmacology, pp. 9642-9647.
Christensen G.L., "Sequential Versus Combined Treatment of Human Breast Cancer Cells with Anliestrogens and the Vitamin D Analogue EB 1089 and Evaluation of Predictive Markers for Vitamin D Treatment", Breast Cancer Researcr and Treatment 85(1) 53-63 (2004).
Clement et al.., "Three dimensional pharmacophore modeling of human CYP17 inhibitors. Potential agents for prostate cancer therapy", journal of Medicinal Chemistry, vol. 46, No. 12, 2003, pp. 2345-2351.
Clinical Cancer Research, "A Journal of the American Association for Cancer Research", Letter to Ian Judson, RE: "Manuscript# 030579, Hormonal impact of the 17a-hydroxylase/C17, 20-lyase inhibitor abiraterone acetate (CB7630) in patients with prostate cancer", Filed for case IPR2016-01332, Janssen Exhibit 2030, on May 12, 2003, 4 pages.
Clinical trial patient data extract, for Patient 1, Patient 2, 2007, 2 pages.
ClnicalTrials.gov, "Phase II Clinical Trial of Ablraterone Acetate Without Exogenous Glucocorticoids in Men With Castrationresistant

(56) References Cited

OTHER PUBLICATIONS

Prostate Cancer With Correlative Assessment of Hormone Intermediates.", NCT02025010, *Amerigen* v. *Janssen*, Case# IPR2016-00286. 5 pages.
Cole, "Cancer Expert Doubts Claims About Prostate Cancer Trial," BMJ, vol. 337: a979 (2008).
Coligar Biotechnology, Cougar Biotechnology presents C87630 Phase I clinical data at the 2005 Prostate Cancer Symposium, All Business, 2005.
Collette et al., Is Prostate-Specific Antigen a Valid Surrogate End Point for Survival in Hormonally Treated Patients With Metastatic Prostate Cancer? Joint Research of the European Organization fur Research and Treatment of Cancer, the Limburgs Universitair Centrum, and AstraZeneca Pharmaceuticals, Journal of Clinical Oncology, vol. 23, No. 25, pp. 6139-6148 (Sep. 1, 2005).
Collette et al., Prostate-specific antigen (PSA) alone is not an appropriate surrogate marker of long-term therapeutic benefit in prostate cancer trials, European Journal of Cancer, 42, pp. 1344-1350 (2006).
Collins et al.., "A systematic review of the effectiveness of docetaxel and mitoxantrone for the treatment of metastatic hormone-refradory prostate cancer," British J. of Cancer. 95, pp. 457-462 (2006).
Colston et al., "Mechanisms implicated In the growth regulatory effects of vitamin D In breast cancer," Endocrine-Related Cancer, vol. 9(1):45-59 (2001).
Colston, K. W., "Effects of Seocalcitol (EB1089) on Nitrosomethyl Urea-Induced Rat Mammary Tumors", 80(3) Breast Cancer, 303•311 (2003).
Conde and Aronson, "Risk factors for male osteoporosis." Urologic Oncology, Seminars and Original Investigations, Filed fur Case IPR2016-00286, Janssen Exhibit 2025. on 2003, vol. 21, pp. 380-383.
Consider the impact of Zvtiga (Registered) 500 mg film-coated tablets over the course of a month or a year for your patients with mCRPC, Zvtiga (Registered) (abiraterone acetate) Dosing & Monitoring HCP 7 pages.

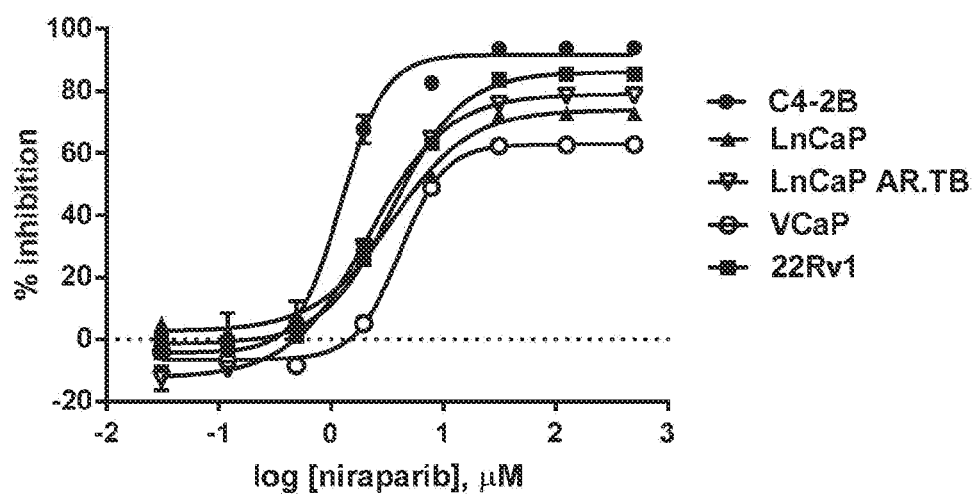
Figure 1. Niraparib inhibits the growth of human prostate tumor cell lines in vitro.

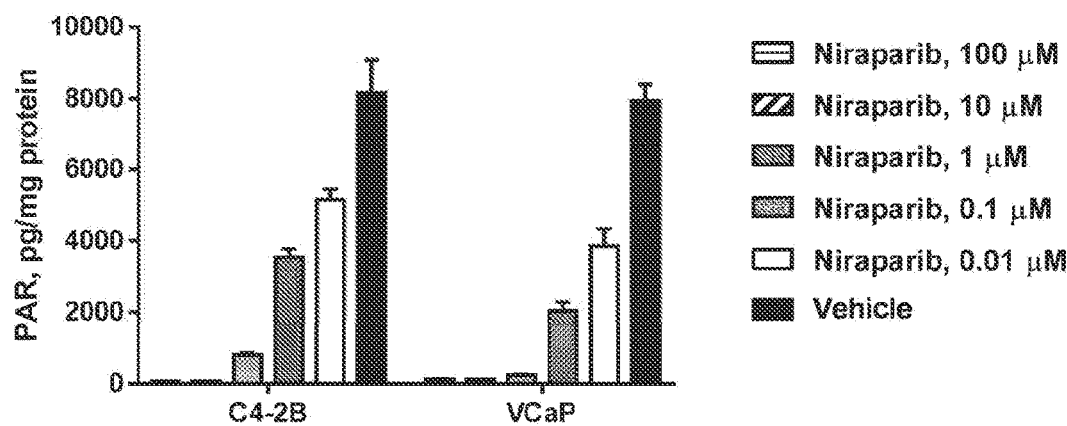
Figure 2. Niraparib suppresses PAR formation in two human prostate tumor cell lines in vitro.

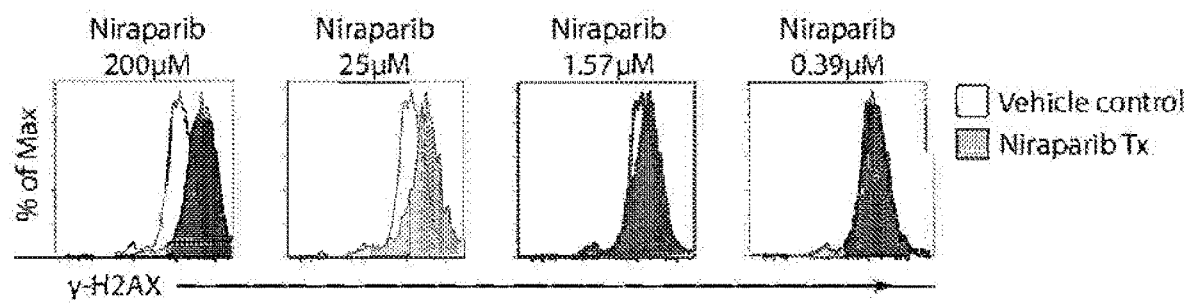
Figure 3. Niraparib treatment induces increased γ-H2AX in 22RV1 cells in a dose-dependent manner, as measured by flow cytometry.

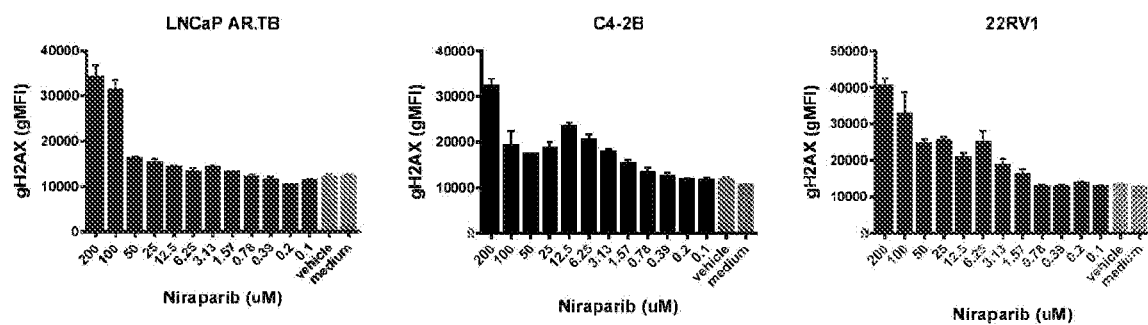
Figure 4. Niraparib induces γ-H2AX in 22RV1, LNCaP AR-TB, and C4-2B cells in vitro.

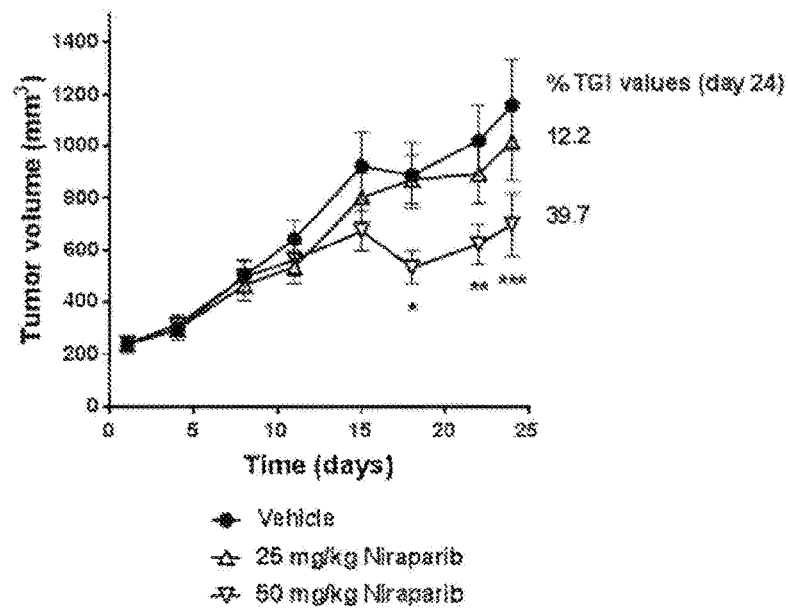
Figure 5. Niraparib treatment inhibits growth of C4-2B-luc prostate tumors in NSG male mice.

METHODS OF TREATING PROSTATE CANCER

CROSS-REFERENCE TO RELATED APPLICATIONS

The present application is a continuation of U.S. patent application Ser. No. 17/989,329, filed Nov. 17, 2022, which is a continuation of U.S. patent application Ser. No. 17/528,017, filed Nov. 16, 2021, which is a continuation of U.S. patent application Ser. No. 16/131,772, filed Sep. 14, 2018, now U.S. Pat. No. 11,207,311, which is a continuation of U.S. patent application Ser. No. 15/663,082, filed Jul. 28, 2017, which claims the benefit of U.S. Provisional Application No. 62/368,466, filed on Jul. 29, 2016, and U.S. Provisional Application No. 62/369,239, filed on Aug. 1, 2016, all of which are incorporated herein by reference in their entireties.

FIELD OF THE INVENTION

The present invention relates to the treatment of metastatic hormone-naïve prostate cancer in a human by administering a safe and/or an effective amount of niraparib to such human.

BACKGROUND OF THE INVENTION

Prostate cancer is the most common non-cutaneous malignancy in men and the second leading cause of death in men from cancer in the western world. Prostate cancer results from the uncontrolled growth of abnormal cells in the prostate gland. Once a prostate cancer tumor develops, androgens, such as testosterone, promote prostate cancer tumor growth. At its early stages, localized prostate cancer is often treated with local therapy including, for example, surgical removal of the prostate gland and radiotherapy. However, when local therapy fails to cure prostate cancer, as it does in up to a third of men, the disease progresses into incurable metastatic disease (i.e., disease in which the cancer has spread from one part of the body to other parts).

Treatment of metastatic prostate cancer Androgen deprivation therapy ("ADT") or androgen suppression therapy is performed to reduce the testicular production of testosterone. ADT includes surgical castration (orchiectomy) or the use of luteinizing hormone-releasing hormone ("LHRH") antagonists or agonists. Examples of LHRH antagonists include degarelix. Examples of LHRH agonists include goserelin acetate, histrelin acetate, leuprolide acetate, and triptorelin palmoate.

Abiraterone acetate is a prodrug of abiraterone, inhibits 17α hydroxylase/C17, 20-lyase (cytochrome P450c17 [CYP17]), a key enzyme in androgen biosynthesis. Abiraterone acetate in combination with prednisone has been approved for the treatment of men with metastatic castration-resistant prostate cancer ("mCRPC") who have received prior chemotherapy containing docetaxel. The efficacy and safety of abiraterone acetate (1,000 mg daily tablet dose) and prednisone (5 mg twice daily) therapy in patients with mCRPC is established by the results of COU-AA-301 and COU-AA-302, both Phase 3, multinational, randomized, double-blind, placebo-controlled studies. Study COU-AA-301 was the first Phase 3 study to demonstrate that further lowering testosterone concentrations below that achieved with androgen deprivation therapy ("ADT") using CYP17 inhibition with abiraterone acetate improves survival in patients with mCRPC. COU-AA-302 demonstrated significantly improved overall survival ("OS") and radiographic progression-free survival ("rPFS") in chemotherapy-naïve patients with mCRPC treated with abiraterone acetate plus prednisone compared with placebo plus prednisone.

What is needed are data to determine whether abiraterone acetate in combination with low-dose prednisone and ADT is superior to ADT alone in improving rPFS and OS in subjects with mHNPC with high-risk prognostic factors.

Thus, the treatment of prostate cancer, including castrate resistant prostate cancer and metastatic castrate resistant prostate cancer, by way of PARP inhibition with niraparib in mCRPC patients, including those with DNA-repair anomalies. This treatment may follow chemotherapy or may be a chemo-naïve subject. This treatment may follow AR-targeted agents, e.g., enzalutamide, apalutamide, and bicalutamide. Therefore, niraparib may present another treatment option.

SUMMARY OF THE INVENTION

The present invention is directed to a method for treating prostate cancer in a human in need of such treatment comprising, consisting of, and/or consisting essentially of administering to the human a therapeutically effective amount of niraparib.

In an embodiment, the present invention is directed to a method of treating prostate cancer in a human in need of such treatment comprising, consisting of, and/or consisting essentially of administering to the human a therapeutically effective amount of niraparib, wherein the prostate cancer is castration-resistant prostate cancer ("CRPC"), metastatic castration-resistant prostate cancer, and/or antiandrogen-resistant prostate cancer.

In another embodiment, the present invention is directed a method for treating prostate cancer in a human in need of such treatment comprising, consisting of and/or consisting essentially of administering niraparib to a human, wherein the human is carrying at least one DNA repair anomaly selected from the group consisting of BRCA-1, BRCA-2, FANCA, PALB2, CHEK2, BRIP1, HDAC2, and ATM.

In another embodiment, the present invention is directed a method for treating prostate cancer in a human in need of such treatment comprising, consisting of and/or consisting essentially of administering niraparib to a human, wherein the human is carrying at least one DNA repair anomaly that is either BRCA-1 or BRCA-2.

In another embodiment, the present invention is directed to a method of treating prostate cancer in a human in need of such treatment comprising, consisting of, and/or consisting essentially of administering to the human niraparib in an amount of, preferably, from about 30 mg/day to about 400 mg/day, more preferably 300 mg/day, and most preferably once daily oral administration in three 100 mg oral dosage forms.

In another embodiment, the present invention is directed to a composition comprising niraparib for the treatment of prostate cancer, antiandrogen resistant prostate cancer, castration-resistant prostate cancer, and metastatic castration-resistant prostate cancer.

BRIEF DESCRIPTION OF THE DRAWINGS

FIG. 1. Illustrates that niraparib inhibits the growth of human prostate tumor cell lines in vitro.

FIG. 2. Illustrates that niraparib suppresses PAR formation in two human prostate tumor cell lines in vitro.

FIG. 3. Illustrates that niraparib treatment induces increased γ-H2AX in 22RV1 cells in a dose-dependent manner, as measured by flow cytometry.

FIG. 4. Illustrates that niraparib induces 7-H2AX in 22RV1, LNCaP AR-TB, and C4-2B cells in vitro.

FIG. 5. Illustrates that niraparib treatment inhibits growth of C4-2B-luc prostate tumors in NSG male mice.

DETAILED DESCRIPTION OF THE INVENTION

The term "subject" refers to a mammal, most preferably a human, who has been or is the object of treatment, observation or experiment.

The term "treatment" refers to the treatment of a subject afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically effective amount" refers to an amount of niraparib that elicits the biological or medicinal response in a tissue system that is being sought by a researcher, veterinarian, medical doctor or other clinician, which includes alleviation or partial alleviation of the symptoms of the disease, syndrome, condition, or disorder being treated.

The term "safe and effective amount" refers to an amount of niraparib that elicits the prevention or amelioration of disease progression and acceptable toxicity in the human.

The term "composition" refers to a pharmaceutical product that includes the specified ingredients sometimes in therapeutically effective amounts, as well as any product that results, directly, or indirectly, from combinations of the specified ingredients in the specified amounts.

The term "pharmaceutically acceptable" as used herein pertains to compound, materials, compositions and/or dosage forms that are, within the scope of sound medical judgement, suitable for use in contact with the tissues of a human without excessive toxicity, irritations, allergic response, or other problem or complication, commensurate with a reasonable benefit/risk ratio. Each carrier, excipient, etc. must all be "acceptable" in the sense of being compatible with the other ingredients of the formulation.

The term "androgen receptor" as used herein is intended to include the wild-type androgen receptor as well as androgen-resistant ARs and/or AR mutants associated with castration-resistant prostate cancer.

As used herein, the term "antiandrogen" refers to a group of hormone receptor antagonist compounds that is capable of preventing or inhibiting the biologic effects of androgens on normally responsive tissues in the body. In some embodiments, an anti-androgen is a small molecule. Antiandrogens include enzalutamide, apalutamide, and abiraterone acetate.

As used herein, the term "first-generation anti-androgen" refers to an agent that exhibits antagonist activity against a wild-type AR polypeptide. However, first-generation anti-androgens differ from second-generation anti-androgens in that first-generation anti-androgens can potentially act as agonists in CRPC.

Exemplary first-generation anti-androgens include, but are not limited to, flutamide, nilutamide and bicalutamide.

As used herein, the term "second-generation anti-androgen" refers to an agent that exhibits full antagonist activity against a wild-type AR polypeptide. Second-generation anti-androgens differ from first-generation anti-androgens in that second-generation anti-androgens act as full antagonists in cells expressing elevated levels of AR, such as for example, in CRPC. Exemplary second-generation anti-androgens include 4-[7-(6-cyano-5-trifluoromethylpyridin-3-yl)-8-oxo-6-thioxo-5,7-diazaspiro[3.4]oct-5-yl]-2-fluoro-N methylbenzamide (also known as ARN-509; CAS No. 956104-40-8); 4-(3-(4-cyano-3-(trifluoromethyl)phenyl)-5,5-dimethyl-4-oxo-2-thioxoimidazolidin-1-yl)-2-fluoro-N-methylbenzamide (also known as MDV3100 or enzalutamide; CAS No: 915087-33-1) and RD162 (CAS No. 915087-27-3). In some embodiments, a second-generation anti-androgen binds to an AR polypeptide at or near the ligand binding site of the AR polypeptide.

As used herein, the term "third-generation anti-androgen" refers to an agent that exhibits full antagonist activity against a wild-type AR polypeptide and against mutant forms of the AR polypeptide, with mutations arising in the ligand binding domain (LBD) of the AR polypeptide as set forth below. Third-generation anti-androgens retain the differentiation from first-generation anti-androgens in that third-generation anti-androgens act as full antagonists in cells expressing elevated levels of AR, such as for example, in CRPC.

As used herein, the term "mutant" refers to an altered (as compared with a reference) nucleic acid or polypeptide, or to a cell or organism containing or expressing such altered nucleic acid or polypeptide.

As used herein, unless otherwise noted, the term "affect" or "affected" (when referring to a disease, syndrome, condition or disorder that is affected by antagonism of AR) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

Embodiments of the present invention include prodrugs of niraparib. In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound hi vivo after administration to a patient. Conventional procedures for the selection and preparation of suitable prodrug derivatives are described, for example, in "Design of Prodrugs", ed. H. Bundgaard, Elsevier, 1985.

Androgen Receptor (AR)

Androgens bind to a specific receptor, the androgen receptor (AR), inside the cells of target tissues. The AR is expressed in numerous tissues of the body and is the receptor through which the physiological as well as the pathophysiological effects of endogenous androgen ligands, such as testosterone (T) and dihydrotestosterone (DHT), are expressed. Structurally, the AR is composed of three main functional domains: the ligand binding domain (LBD), the DNA-binding domain, and amino-terminal domain. A compound that binds to the AR and mimics the effects of an endogenous AR ligand is referred to as an AR agonist, whereas a compound that inhibits the effects of an endogenous AR ligand is termed an AR antagonist. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue. In the prostate, androgens stimulate the growth of prostate tissue and prostate cancer cells by binding to the AR that is present within the cytoplasm of androgen sensitive tissue.

Compounds that selectively modulate AR are of clinical importance in the treatment of or prevention of a variety of diseases, conditions, and cancers, including, but not limited to, prostate cancer, benign prostatic hyperplasia, hirsutism in women, alopecia, anorexia nervosa, breast cancer, acne, musculoskeletal conditions, such as bone disease, hematopoietic conditions, neuromuscular disease, rheumatological disease, cancer, AIDS, cachexia, for hormone replacement therapy (HRT), employed in male contraception, for male performance enhancement, for male reproductive conditions, and primary or secondary male hypogonadism.

Castration Resistant Prostate Cancer

Agents that block the action (antiandrogens) of endogenous hormones (e.g., testosterone) are highly effective and routinely used for the treatment of prostate cancer (androgen ablation therapy). While initially effective at suppressing tumor growth, these androgen ablation therapies eventually fail in almost all cases, leading CRPC. Most, but not all, prostate cancer cells initially respond to androgen withdrawal therapy. However, with time, surviving populations of prostate cancer cells emerge because they have responded to the selective pressure created by androgen ablation therapy and are now refractory to it. Not only is the primary cancer refractory to available therapies, but cancer cells may also break away from the primary tumor and travel in the bloodstream, spreading the disease to distant sites (especially bone). This is known as metastatic castration resistant prostate cancer ("mCRPC"). Among other effects, this causes significant pain and further bone fragility in the subject.

In some embodiments, the subject's prostate cancer is resistant to or non-responsive to antiandrogen treatment, including, but not limited to, enzalutamide, apalutamide and abiraterone acetate ("antiandrogen resistance").

The preparation of niraparib, 2-[4-[(3S)-piperidin-3-yl]phenyl]indazole-7-carboxamide, may be found in U.S. Pat. No. 8,071,623, issued on Dec. 6, 2011 and entitled Amide Substituted Indazoles as Poly(ADP-Ribose)Polymerase (PARP) Inhibitors, which claims the benefit of U.S. provisional patent application No. 60/921,310, filed on Feb. 16, 2010, as well as U.S. Pat. No. 8,436,185, issued on May 7, 2013 and entitled Pharmaceutically Acceptable Salts of 2-[4-[(3S)-piperidin-3-yl]phenyl]-2H-indazole-7-carboxamide, which claims the benefit of U.S. provisional patent application No. 61/010,333 filed on Jan. 8, 2008; each of which is incorporated herein by reference.

The invention also provides pharmaceutical compositions comprising niraparib and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium croscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water-soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water-soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanal, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachisoil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant. The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Niraparib may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the instant compounds are employed. (For purposes of this application, topical application shall include mouth washes and gargles.)

Niraparib can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Niraparib may also be delivered as a suppository employing bases such as cocoa butter, glycerinated gelatin, hydrogenated vegetable oils, mixtures of polyethylene glycols of various molecular weights and fatty acid esters of polyethylene glycol.

When niraparib is administered to a subject, the selected dosage level will depend on a variety of factors including, but not limited to, the activity of the particular compound, the severity of the individual's symptoms, the route of administration, the time of administration, the rate of excretion of the compound, the duration of the treatment, other drugs, compounds, and/or materials used in combination, and the age, sex, weight, condition, general health, and prior medical history of the patient. The amount of niraparib and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of niraparib is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

A therapeutically effective amount of niraparib or a pharmaceutical composition thereof for the treatment of prostate cancer includes a dose range from about 30 mg/day to about 400 mg/day of niraparib, or any particular amount or range therein, in particular about 300 mg/day, and once daily oral administration in three 100 mg oral dosage forms. Optimal dosages of niraparib to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Niraparib may be administered in any of the foregoing compositions and dosage regimens or by means of those compositions and dosage regimens established in the art whenever use of niraparib is required for a subject in need thereof.

EXAMPLES

The following Examples are set forth to aid in the understanding of the invention, and are not intended and should not be construed to limit in any way the invention set forth in the claims which follow thereafter.

Example 1

In Vitro Cytotoxicity of Niraparib in Human Prostate Tumor Lines

The cytotoxicity of niraparib was tested in several human prostate tumor lines in vitro. None of the tumor lines is known to be BRCA-1 or BRCA-2 deficient.

Methods:

In vitro cytotoxicity of niraparib was assessed in 5 human prostate cancer cell lines: C4-2B, LNCaP, LNCaP AR.TB, VCaP, and 22Rv1. C4-2B, LNCaP, LNCaP AR.TB, and 22Rv1 cell lines were grown in RPMI1640±GlutaMAX™-I medium (Life Technologies #61870-036) supplemented with 10% heat-inactivated fetal bovine serum (FBS) (Life Technologies 416140-071) and non-essential amino acids (NEAA) (Life Technologies #11140-050); and VCaP cells were grown in DMEM+GlutaMAX™-I medium (Life Technologies ##10569-010) with 10% FBS and NEAA. VCaP cells were subcultured every 7 days; other lines were split every 3-4 days.

Cell growth kinetics of each cell line were determined by seeding cells at several densities and monitoring growth at intervals up to 7 days. Growth was determined using the Promega Cell TiterGlo reagent (#G7571) to measure cellular ATP by means of a chemiluminescent luciferin-luciferase reaction. Plates were read on a Perkin-Elmer Envision plate reader, and luminescence values were plotted in order to identify seeding densities that resulted in log-phase growth and a cell density within the linear range of the Cell TiterGlo assay at the desired time point.

For niraparib cytotoxicity experiments, cells were harvested by brief trypsinization and each line was seeded to the inner 60 wells of 96-well plates in 100 µL of medium at an appropriate density for a 7-day treatment. The outer wells of each plate were filled with Dulbecco's phosphate buffered saline (DPBS; Life Technologies #14190-144) to reduce evaporation from test wells. Cells were rested overnight in the plates at 37° C. in a humidified 5% $CO_2$ incubator. Treatment was initiated by addition of 50 µL of 3× niraparib (final concentrations 500, 125, 31.3, 7.8, 1.95, 0.49, 0.12, 0.03 µM) in the appropriate medium to triplicate wells. The final vehicle concentration was 0.5% DMSO.

Cells were cultured for 7 days. Relative cell viability after treatment was determined using Cell TiterGlo reagent, as above. All luminescent output values were normalized to percent inhibition based on mean luminescence of the untreated control wells, and the mean percent inhibition of the vehicle control wells was subtracted from each treatment value. Percent inhibition was plotted vs log µM concentration in GraphPad Prism 7.00. Nonlinear regression and calculation of $EC_{50}$ values were performed using the log (agonist) vs. response—Variable slope (four parameters) fit.

Results:

Results of the cytotoxicity assay are shown in FIG. 1 and Table 1. Growth of each cell line was reduced in a dose-dependent fashion by increasing concentrations of niraparib. C4-2B cells appeared to be the most sensitive, with an $EC_{50}$ value of ~1.2 µM. VCaP cells appeared to be the least sensitive with an $EC_{50}$ value of 4.1 µM.

TABLE 1

$EC_{50}$ values for 7-day niraparib treatment of human prostate tumor celllines.

| Cell Line | $EC_{50}$, µM |
|---|---|
| C4-2B | 1.222 |
| LNCaP | 3.502 |
| LNCaP AR.TB | 2.140 |
| VCaP | 4.099 |
| 22Rv1 | 3.517 |

Example 2

Inhibition of PAR Formation by Niraparib

The ability of niraparib to inhibit the formation of poly (ADP)ribose (PAR) was tested in two human prostate tumor lines in vitro. Neither of the tumor lines is known to be BRCA-1 or BRCA-2 deficient.

Methods:

PAR inhibition using niraparib was assessed in 2 human prostate cancer cell lines, C4-2B and VCaP. The C4-2B cell line was grown in RPMI1640±GlutaMAX™-I medium supplemented with 10% FBS and NEAA and split every 3-4 days. VCaP cells were grown in DMEM+GlutaMAX™-I medium with FBS and NEAA and subcultured every 7 days.

Cells were harvested by brief trypsinization and each line was seeded into 6-well plates in 1 mL of medium at an appropriate density. An extra 500 µL of complete medium was added, for a total volume per well of 1.5 mL. Cells were rested overnight in the plates at 37° C. in a humidified 5% $CO_2$ incubator. The next day, medium was removed from plates and cells were washed using 1 mL serum free medium (RPMI or DMEM respectively). Treatment was initiated by addition of 1 mL of niraparib (final concentrations 100, 10, 1, 0.1, 0.01 and 0 µM in 0.1% DMSO) in the appropriate medium to triplicate wells. Plates were returned to the incubator for two hours.

Following treatment, extracts were prepared using reagents and procedures provided in the HT PARP in vivo Pharmacodynamic Assay II (Trevigen #4520-096-K). Medium was removed from each well and placed into separate labeled microfuge tubes, and the plates were placed on ice. The tubes were spun at 1500 rpm for 4 minutes to pellet any cells that detached from the plate during drug incubation. Lysis buffer was prepared using 24.5 mL of cell lysis reagent with 250 µL of 100 mM PMSF (in ethanol; Sigma #93482) and 250 µL 100× Protease Inhibitor Cocktail (Thermo Scientific #78429). Lysis buffer (300 µL) was added to each well of the plates, on ice. Adherent cells were scraped into lysis buffer and kept on ice for at least 15 minutes. Supernatant was removed from the microfuge tubes, and the cell lysates from the 6-well plates were added to each tube from the corresponding tubes. SDS (20% w/v) was added to bring the final SDS concentration to 1%. The cell extracts were heated to 95-100° C. for 5 minutes. After cooling to room temperature, 0.01 volume of 100× magnesium cation and 3 µL DNase were added to each tube. Tubes were briefly vortexed and returned to a 37° C. incubator for 90 minutes. After the incubation, tubes were centrifuged at 10,000×g for 10 minutes at room temperature. If a pellet was present, it was removed using a pipette tip and extracts were transferred to a 96 well dilution plate. Cell extracts were frozen at −80° C. until used for protein quantitation and the PAR ELISA assay. The ELISA assay protocol was performed according to the manufacturer's instructions.

Protein quantitation was performed using the detergent-compatible Biorad DC protein assay kit II (#500-0002) with the Biorad Quick Start Bovine Serum Albumin Standard Set (#5000207) according to the manufacturer's 96-well plate protocol. ELISA lysis buffer was spiked into the standards, and an equal volume of PBS was added to all sample wells to correct for any effect of the lysis buffer on protein readings. Samples were assayed in duplicate. Buffer A' (25 µL) was added to all wells of the plate, and 200 xL of Buffer B was immediately added to each well. Plates were incubated for 15 minutes at room temperature on a shaker. Absorbance was read at 750 nm on a Molecular Devices M5 plate reader, using the DC Protein Assay protocol in SoftMax Pro version 6.3 software. Linear regression of the standard curve, interpolation of sample protein values, and replicate averaging were performed in the software. Data was exported to Excel, where any corrections for sample dilution were performed.

Luminescence values of PAR ELISA standards and samples were analyzed in GraphPad Prism version 7, where linear regression of the standard curve and interpolation of sample values were calculated. Interpolated PAR values (pg PAR/mL) were corrected for sample dilution and divided by the corresponding protein concentration to yield pg PAR/mg of protein. These values were graphed in GraphPad Prism v7.

Results:

The results from the PAR assay are shown in FIG. 2. PAR was reduced in a dose-dependent fashion by increasing concentrations of niraparib in each cell line.

Example 3

Niraparib Induces γ-H2AX in Human Prostate Tumor Lines In Vitro

The ability of niraparib to induce double stranded breaks in DNA was measured in 3 human prostate cancer cell lines 22RV1, LNCaP AR.TB, and C4-2B. Double stranded breaks in DNA are followed by phosphorylation of adjacent histone γ-H2AX, and this phosphorylation can be measured by antibody staining and flow cytometry.

Methods:

22RV1, LNCaP AR.TB, and C4-2B cell lines were grown as outlined above. Cell lines were passaged every 3-4 days.

For each cell line, $2 \times 10^5$ cells were seeded in each well of a 12-well plate (Falcon 4353043) in a volume of 1 mL of media. Cells were rested overnight in a 37° C. humidified 5% $CO_2$ incubator, then 1 nil, of media containing 2× concentrated serially diluted niraparib was added to achieve final concentrations of 200, 100, 50, 25, 12.5, 6.25, 3.13, 1.57, 0.78, 0.39, 0.2, and 0.1 µM in triplicate wells. The final vehicle concentration was DMSO and triplicate wells of vehicle and media controls were also obtained for each cell line. Plates were incubated for another 18 hours.

Following the 18 hour incubation with drug, each well of cells was harvested by first transferring the 2 mL of media into a 15 mL conical tube (Corning #430798). 500 µL of cell dissociation buffer (Gibco #13151-014) was then added to the well and allowed to sit for 5 minutes. Using a 1 mL pipette, 1 mL of media was added to the well, cells were dislodged by pipetting, and the cell-containing media was transferred to the corresponding nil, conical tube. Tubes were centrifuged at 1200 rpm for 5 minutes, the supernatant was discarded, and the pelleted cells were resuspended and transferred to a 96-well v-bottom plate (Costar #3896). Plates were centrifuged at 1800 rpm for 3 minutes, supernatant discarded, then wells were washed with 200 uL of DPBS. This process was repeated for a total of 3 washes. Cells were then stained with 100 uL of DPBS containing a 1:800 dilution of Invitrogen Live/Dead fixable aqua (Invitrogen #L34957) for 20 minutes at 4° C. Cells were then washed with 150 µL BD Pharmingen Stain Buffer (stain buffer; BD #554657) and centrifuged at 1800 rpm for 3 minutes. Cells were washed again 2 times with 200 µL stain buffer and then once with DPBS.

Cells were fixed with 100 µL −20° C. 70% ethanol/$H_2O$ and plates were stored at −20° C. for 2 hours. Cells were washed 3 times with stain buffer centrifuging at 2200 rpm for 3 minutes between each wash. Cells were then incubated with 100 µL of a 1:1 dilution stain buffer and AXELL biotin-free Fc receptor blocker (Accurate Chemical & Scientific Corp #NB309) for 20 minutes at 4° C. Cells were washed with 150 of stain buffer then centrifuged at 2200 rpm for 3 minutes, supernatant discarded, then cells were incubated with 50 µL stain buffer containing 0.2% v/v Triton X-100 (Acros Organics #21568-2500) for 2 hours at room temperature in the dark along with 1:100 dilutions of γ-H2AX antibody (Biolegend #613408).

Cells were washed once with 200 EEL stain buffer containing 0.2% v/v Triton X-100, and then washed once with 200 µL stain buffer only. Cells were resuspended in 80 µL of stain buffer and 50 µL was analyzed on a BD Fortessa flow cytometer. Data were analyzed using TreeStar FlowJo v9.8.5. Data was gated on live cells, then following doublet discrimination, the entire population was assessed for γ-H2AX antibody signal. Results were graphed In GraphPad Prism v7.

Results:

Representative histograms for the 22RV1 cell line are shown in FIG. 3, depicting the effect of different concentrations of niraparib. Drug-treated samples were compared to vehicle and media controls and are graphed in FIG. 4. The lowest concentrations where γ-H2AX signal rises significantly above vehicle control are indicated in Table 2. The results show that, in each prostate tumor line, niraparib induces γ-H2AX in a dose-dependent manner.

TABLE 2

| Minimum concentration of niraparib that induces significant change in γ-H2AX | |
|---|---|
| Cell line | 1$^{st}$ Significant Concentration (µM) |
| 22AV1 | 1.57 |
| LnCaP.AR.TB | 3.13 |
| C4-28 | 1.57 |

Example 4

Niraparib Inhibits the Growth of C4-2B Human Prostate Tumors in Mice

The activity of niraparib was tested in the pre-established human prostate subcutaneous C4-2B model in non-obese diabetic (NOD) severe combined immunodeficient (scid) gamma (NOD.Cg-Prkdc Il2rg/SzJ) (NSG) mice. This tumor model is not believed to be BRCA-1 or BRCA-2 deficient.

Methods:

Vehicle was 0.5% Methyl cellulose (Methocel™ F4M) prepared and kept at 4° C. in the dark. All formulations were made to be dosed at a volume of 10 ml/kg body weight. NSG male mice (Jackson Laboratories) were used. Animals were habituated for one week prior to any experimental procedures being performed. Mice were group housed (5 per cage) in disposable IVC-cages (Innovive, San Diego, CA, USA) under a 12-h light:dark cycle at a temperature of 19 to 22° C. and 35 to 40% humidity. Mice were fed an autoclaved high fat (6%) diet laboratory chow and water ad libitum.

Mice were injected with LNCaP C4-2B-luc tagged cells ($1\times10^6$ tumors cells in a 200 µl volume of Cultrex®:RPMI 1640 medium (1:1 ratio) on the right flank. Mice were randomized per tumor volumes (tumor volume=241±14 mm$^3$), with 10 mice per treatment group. Mice were dosed daily by gavage (p.o.) with either vehicle, or vehicle containing niraparib as indicated below at 10 ml/kg dosing volume. Start of treatment=Day 1. Mice were treated through study day 24.

| | |
|---|---|
| Group 1 | 0 mg/kg Vehicle (0.5% Methocel F4M) dosed QD p.o. |
| Group 2 | 25 mg/kg niraparib in 0.5% Methocel F4M dosed QD p.o. |
| Group 3 | 50 mg/kg niraparib in 0.5% Methocel F4M dosed QD p.o. |

For each individual animal, body weight and tumor volume [using the formula: Tumor Volume (mm3)=$(a\times b^2/2)$; where 'a' represents the length, and 'b' the width of the tumor as determined by caliper measurements], were monitored twice weekly throughout the study. For the pre-established tumors, a time-course of tumor growth is expressed as mean±standard error of the mean (SEM).

Results:

The vehicle treated mice started to reach ethical limits for tumor volume around study day 22 onwards (see FIG. 5 for individual tumor volumes). Tumor volume data was presented up to study day 24 (when 9 of 10 vehicle-treated mice remained on study). After 18, 22, and 24 days of treatment, group 3 dosed daily with 50 mg/kg niraparib p.o. showed significant inhibition/delay in tumor growth, with tumor growth inhibition (TGI) values of ~40% on these days. Significant differences in tumor growth were observed on days 18, 22 and 24 (*$p<0.05$; $p<0.01$; *$p<0.001$). Mice dosed at 25 mg/kg of niraparib did not show significant tumor growth inhibition, though there was modest TGI of ~12% on days 22 and 24.

Example 5

A multicenter, open-label study is carried out to assess the efficacy and safety of once daily dosing of 300 mg niraparib in male subjects over the age of 18 years with mCRPC and DNA-repair anomalies who have had at least one line of taxane-based chemotherapy and at least one line of antiandrogen therapy (e.g., abiraterone acetate, enzalutamide, apalutamide). The study will enroll approximately 100 subjects. Subjects will be monitored for safety during the study period, and up to 30 days after the last dose of study drug. Treatment will continue until disease progression, unacceptable toxicity, death, or the sponsor terminates the study.

The study will consist of 4 phases; a Prescreening Phase for biomarker evaluation only, a Screening Phase, a Treatment Phase, and a Follow-up Phase. The efficacy evaluations include the following: Tumor measurements: chest, abdomen and pelvis CT or MRI scans and whole body bone scans ($^{99mTc}$), serum PSA, survival status, CTC, and symptomatic skeletal event (SSE).

Niraparib, 300 mg, will be provided as capsules (3×100 mg) for once daily oral administration. The capsules must be swallowed whole. Subjects should take their dose in the morning (with or without food). Although not considered study medication, subjects who have not undergone surgical castration must continue to receive regularly prescribed GnRHa. All GnRHa therapies should be recorded in the concomitant medication section of the eCRF.

A treatment cycle is defined as 28 days. Subjects will begin taking niraparib on Day 1 of Cycle 1. Sufficient quantities of niraparib for each treatment cycle will be distributed on the first day of each cycle. If subjects miss a dose, then that dose should be replaced if the subject remembers within an approximate 12-hour window. Otherwise, subjects should take the next dose the following day, without compensating for the missed dose. Missed doses should be recorded in the eCRF.

Prescreening Phase for Biomarker Evaluation

The Prescreening Phase will evaluate if a potential subject is biomarker-positive for DNA-repair anomalies. All subjects will be required to sign a specific ICF for the Prescreening Phase and provide baseline demographic characteristics and disease-specific medical history. The Prescreening Phase may occur any time prior to the Screening Phase.

The process for determining biomarker-positivity will be different for subjects who enter the Prescreening Phase before a blood-based assay is available, compared with those subjects who enter after a blood-based assay is available. The 2 processes are described below.

Process for Determining Biomarker-Positivity Before a Blood-Based Assay is Available The Subject signs the prescreening ICF. If the subject has had tumor tissue previously analyzed by the FoundationOne® gene panel, then after the subject grants a release, the FoundationOne® data can be reviewed to determine eligibility based on the criteria defined in Table 1 If the subject is biomarker-positive, they are eligible to enter the Screening Phase. If the subject has not had tumor tissue previously analyzed by the FoundationOne® gene panel, then they must have either archival or recently collected (recommended) tumor tissue analyzed for biomarker-positivity by a sponsor-approved test. If the subject is biomarker-positive, they are eligible to enter the Screening Phase.

Blood samples will also be collected from all subjects during the Prescreening Phase and stored for when a blood-based assay becomes available. At the time a blood-based assay becomes available, the stored blood sample will be analyzed for concordance with the tumor tissue sample results. This analysis may occur at any time after the blood-based assay becomes available.

Process for Determining Biomarker-Positivity after a Blood-Based Assay is Available Subject signs the prescreening ICF. Subject has blood collected and sent for analysis of biomarker-positivity. If the subject has had tumor tissue previously analyzed by the FoundationOne® gene panel, then after the subject grants a release, the FoundationOne® data can be reviewed to determine eligibility based on the criteria defined in Table 1. If the subject is biomarker-positive, they are eligible to enter the Screening Phase and do not need to wait for results of the blood-based analysis. If the FoundationOne® gene panel is negative, the subject may still be considered eligible if they are determined to be biomarker-positive by the blood-based assay. If the subject has not had tumor tissue previously analyzed by the FoundationOne® gene panel and archival tissue is available, then a request for retrieval and analysis of the archived tumor tissue is initiated. If the blood-based assay results are biomarker-positive, then the subject is eligible to enter the Screening Phase and does not need to wait for results of the archival tumor tissue-based analysis. The results from the archival tumor tissue-based analysis, when they are available, may be used in conjunction with the blood-based results for concordance and bridging studies.

At the discretion of the study sponsor, if the blood-based assay results are negative, then the archival tumor tissue-based results may be used to determine eligibility.

If no archival tumor tissue is available, then the subject must agree to have tumor tissue collected.

If the blood-based assay results are biomarker-positive, then the recent tumor tissue must be collected prior to Cycle 1 Day 1 for later use in concordance and bridging studies. Analysis of the recently collected tumor tissue may occur any time during the study and the results may not be required prior to the subject entering the Screening Phase.

At the discretion of the study sponsor, if the blood-based assay results are negative, then the recently collected tumor tissue may be used to determine eligibility.

Once subjects are identified as biomarker-positive during the Prescreening Phase, the Screening Phase should start within 30 days.

Screening Phase

All biomarker-positive subjects must sign the main study ICF prior to the conduct of any study-related procedures in the Screening Phase. During this phase, eligibility criteria will be reviewed and a complete clinical evaluation will be performed as specified in the Time and Events Schedule. Screening procedures will be performed up to 35 days before Cycle 1 Day 1, unless otherwise specified. Imaging will be accepted up to 8 weeks prior to Cycle 1 Day 1. Screening clinical safety laboratory evaluations can be used for Cycle 1 Day 1 assessments if performed within 14 days of Cycle 1.

Subjects who do not meet all inclusion criteria, or who meet an exclusion criterion, may be rescreened once. Rescreening is at the discretion of the investigator and requires sponsor approval and agreement. Subjects who are to be rescreened must sign a new ICF before rescreening. Subjects rescreened within 35 days of planned enrollment may use the initial screening laboratory results, computed tomography (CT)/magnetic resonance imaging (MRI) and bone scans (if still within 8 weeks of Cycle 1 Day 1) to determine eligibility if not the reason for the rescreening.

Treatment Phase

The Treatment Phase will begin at Cycle 1 Day 1 and will continue until the study drug is discontinued. The last measurements taken on Day 1 of Cycle 1 before administration of the study drug or at screening (whichever value was last) will be defined as the baseline values. Visits for each cycle will have a ±3-day window, unless otherwise specified. Study visits will be calculated from the Cycle 1 Day 1 date. Subjects may have imaging performed within ±7 days of visits requiring images. Refer to the Time and Events Schedule for treatment visits and assessments during the Treatment Phase.

For PK and pharmacodynamics sampling days, the subject must not take the study drug at home on the morning of study visits. Study drug should be taken at the site. Details of PK and pharmacodynamics sampling days and times are provided in the Time and Events Schedule. Details of blood sample handling and storage procedures for PK and pharmacodynamics are provided in the laboratory manual.

Clinical evaluations and laboratory studies may be repeated more frequently, if clinically indicated. Study drug treatment will continue until disease progression, unacceptable toxicity, death, or the sponsor terminates the study. Once the subject discontinues study drug, the subject must complete the End-of-Treatment (EoT) visit within 30 days after the last dose of study drug, and enter the Follow-up Phase.

End-of-Treatment Visit

An End of Treatment visit must be scheduled within 30 days after the last dose of study drug or prior to administration of a new anti-prostate cancer therapy, whichever occurs first. If a subject is unable to return to the site for the EoT visit, the subject should be contacted to collect AEs that occurred within 30 days after the last dose of study drug.

Follow-up Phase Once a subject has completed the Treatment Phase, survival follow-up and SSEs will be performed every 3 months either via clinic visits, telephone interview, chart review, or other convenient methods. Deaths regardless of causality and SAEs thought to be related to study drugs will be collected and reported within 24 hours of discovery or notification of the event. If the follow-up information is obtained via telephone contact, then written documentation of the communication must be available for review in the source documents.

Biomarker-Positive Sample for DNA-Repair Anomalies

To evaluate if subjects are biomarker-positive, a blood-based assay may become available during the study that will provide a more rapid method than tissue-based analysis for determining biomarker-positive status, while being more convenient for the subjects. Prior to the blood-based assay becoming available, tumor tissue (either archival or recently collected) will require analysis. To ensure that all subjects, regardless of when they enter the study, have the same biomarker data available for analysis (i.e., for concordance and bridging studies), both tumor tissue and blood samples will be collected from all subjects who sign the prescreening informed consent form (ICF). The process for determining biomarker-positivity will be different for subjects who enter the Prescreening Phase before the blood-based assay is available, compared with those subjects who enter after the blood-based assay is available. However, the status of biomarker-positivity in both tumor tissue and blood will be assessed for all subjects.

To be eligible for the study, subjects must be confirmed biomarker-positive by tumor tissue (either archival or recently collected), or blood testing when available. The biomarkers of interest for this study and the biomarker-positivity criteria are listed in Table 3. Analyses will be performed to define a proxy for bi-allelic loss (e.g., mutation co-expression frequency with copy number loss) and these proxies may be used to determine biomarker-positivity as that information becomes available.

TABLE 3

Biomarker Panel and Criteria for Positivity

| Genes | Definition | Genomic Lesion Required for Positivity |
|---|---|---|
| BRCA-1 | Breast Cancer gene 1 | Homozygous deletion |
| BRCA-2 | Breast Cancer gene 2 | Heterozygous deletion + deleterious mutation |
| FANCA | Fanconi Anemia Complementation Group A gene | Copy neutral loss of heterozygosity + deleterious mutation |
| PALB2 | Partner and Localizer of BRCA2 gene | |
| CHEK2 | Checkpoint Kinase 2 gene | |
| BRIP1 | BRCA1 Interacting Protein C-terminal Helicase 1 gene | |
| HDAC2 | Histone Deacetylase 2 gene | |
| ATM | Ataxia Telangiectasia Mutated gene | |
| ATM | Ataxia Telangiectasia Mutated gene | Mono-allelic deleterious mutation in the kinase catalytic domain |

TABLE 3-continued

Biomarker Panel and Criteria for Positivity

| Genes | Definition | Genomic Lesion Required for Positivity |
|---|---|---|
| | Control Genes | |
| AR | Androgen Receptor gene | |
| TP53 | Tumor Protein 53 gene | |

Mono-allelic loss in all genes will be acceptable for entry into the study until the existing algorithm for bi-allelic loss is validated.

Circulating Tumor Cells

Blood samples will be collected in a Cellsave tube at timepoints specified in the Time and Events Schedule. CTC enumeration will be evaluated at the central laboratory, to assess response to study drug.

Whole Blood for RNA

Whole blood samples will be collected in a Paxgene tube. Multiple ribonucleic acid (RNA) transcripts found in prostate tumors are detectable in the RNA and analysis of these samples will allow evaluation of potential mechanisms of resistance that may emerge with niraparib.

Circulating Tumor DNA

Plasma samples collected during the course of treatment will be used to screen for changes in the levels or types of DNA-repair anomalies observed over time by circulating tumor DNA (ctDNA), and to monitor for potential markers of resistance to niraparib.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method of treating metastatic castration-sensitive prostate cancer in a human in need of such treatment comprising administering to the human a pharmaceutically acceptable amount of niraparib or a salt thereof, wherein the human is carrying at least one DNA repair anomaly in a gene selected from the group consisting of BRCA-1, BRCA-2, FANCA, PALB2, CHEK2, and BRIP1.

2. The method of claim 1, wherein the niraparib or a salt thereof is administered in combination with androgen deprivation therapy.

3. The method of claim 2, wherein the androgen deprivation therapy comprises a luteinizing hormone-releasing hormone antagonist or agonist, or orchiectomy.

4. The method of claim 1, wherein niraparib or a salt thereof is administered in an amount of from about 30 mg niraparib/day to about 400 mg niraparib/day.

5. The method of claim 1, wherein niraparib or a salt thereof is administered in an amount of about 200 mg niraparib/day.

6. The method of claim 1, wherein niraparib or a salt thereof is administered in an amount of about 300 mg niraparib/day.

7. The method of claim 6, wherein niraparib or a salt thereof is administered orally, once daily, in 100 mg niraparib oral dosage forms.

8. The method of claim 1, wherein the human has had at least one line of taxane-based chemotherapy.

9. The method of claim 1, wherein the DNA repair anomaly is a genomic lesion.

10. The method of claim 9, wherein the genomic lesion is a homozygous deletion, heterozygous deletion plus deleterious mutation, or copy neutral loss of heterozygosity plus deleterious mutation.

11. A method of treating metastatic castration-sensitive prostate cancer in a human in need of such treatment comprising administering to the human a therapeutically effective amount of niraparib or a salt thereof, wherein the human is carrying at least one DNA repair anomaly in a gene selected from the group consisting of BRCA-1, BRCA-2, FANCA, PALB2, CHEK2, and BRIP1.

12. The method of claim 11, wherein the niraparib or a salt thereof is administered in combination with androgen deprivation therapy.

13. The method of claim 12, wherein the androgen deprivation therapy comprises a luteinizing hormone-releasing hormone antagonist or agonist, or orchiectomy.

14. The method of claim 11, wherein niraparib or a salt thereof is administered in an amount of from about 30 mg niraparib/day to about 400 mg niraparib/day.

15. The method of claim 11, wherein niraparib or a salt thereof is administered in an amount of about 200 mg niraparib/day.

16. The method of claim 11, wherein niraparib or a salt thereof is administered in an amount of about 300 mg niraparib/day.

17. The method of claim 11, wherein niraparib or a salt thereof is administered orally, once daily, in 100 mg niraparib oral dosage forms.

18. The method of claim 11, wherein the human has had at least one line of taxane-based chemotherapy.

19. The method of claim 11, wherein the DNA repair anomaly is a genomic lesion.

20. The method of claim 19, wherein the genomic lesion is a homozygous deletion, heterozygous deletion plus deleterious mutation, or copy neutral loss of heterozygosity plus deleterious mutation.

21. The method of claim 1, further comprising determining whether the human is carrying at least one DNA repair anomaly in a gene selected from the group consisting of BRCA-1, BRCA-2, FANCA, PALB2, CHEK2, and BRIP1.

22. A method of treating metastatic castration-sensitive prostate cancer in a human in need of such treatment comprising:
   determining whether the human is carrying at least one DNA repair anomaly in a gene selected from the group consisting of BRCA-1, BRCA-2, FANCA, PALB2, CHEK2, and BRIP1, and
   administering to the human a pharmaceutically acceptable amount of niraparib or a salt thereof to a human who is carrying the at least one DNA repair anomaly.

* * * * *